US 7,658,188 B2

(12) United States Patent  (10) Patent No.: US 7,658,188 B2
Halpern et al.  (45) Date of Patent: *Feb. 9, 2010

(54) VOLUME-ADJUSTABLE MANUAL VENTILATION DEVICE

(75) Inventors: Ian Halpern, San Francisco, CA (US); Stephen Ruoss, Redwood City, CA (US)

(73) Assignee: ArtiVent Corporation, San Francisco, CA (US)

( * ) Notice: Subject to any disclaimer, the term of this patent is extended or adjusted under 35 U.S.C. 154(b) by 681 days.

This patent is subject to a terminal disclaimer.

(21) Appl. No.: 11/635,381

(22) Filed: Dec. 6, 2006

(65) Prior Publication Data

US 2007/0169780 A1  Jul. 26, 2007

Related U.S. Application Data

(63) Continuation-in-part of application No. 11/147,070, filed on Jun. 6, 2005, now Pat. No. 7,537,008.

(51) Int. Cl.
*A61M 16/00* (2006.01)
(52) U.S. Cl. ............................. 128/202.28; 128/205.13; 128/203.28
(58) Field of Classification Search ............ 128/200.24, 128/202.28–203.14, 203.22, 204.18, 204.28, 128/205.13–205.17, 898, DIG. 20, 203.28; 601/44, 148–152; 5/702, 710, 713; 297/284.6
See application file for complete search history.

(56) References Cited

U.S. PATENT DOCUMENTS 513,924 A   1/1894  Hartnett
527,248 A  10/1894  North (Continued)

FOREIGN PATENT DOCUMENTS

WO    WO 02/089886    11/2002

(Continued)

OTHER PUBLICATIONS

European Search Report for European Patent Application No. 06772362.7 mailed on Mar. 5, 2009 in 7 pages.

(Continued)

*Primary Examiner*—Steven O Douglas
*Assistant Examiner*—Annette F Dixon
(74) *Attorney, Agent, or Firm*—Knobbe Martens Olson & Bear LLP

(57) ABSTRACT

Disclosed is a manually operable volume-adjustable ventilation device. The device includes a reservoir with an inlet mechanism, an outlet mechanism, and a volume adjuster configured to move a volume adjustment limit of the reservoir and change an expressed maximum volume of the reservoir. The reservoir has a body having a plurality of movable walls defining an enclosed volume. The reservoir has an uncompressed state and a compressed state. The walls of the reservoir are movable with respect to each other, such that moving the walls expresses the volume adjustment limit of the reservoir. The walls can be operably connected by movable structures configured such that two adjacent walls are configured to rotate around substantially orthogonal axes with respect to each other when the reservoir moves from an uncompressed to a compressed state. In some embodiments, the movable structures can be hinges, such as snap-fit assembly hinges. Methods of ventilating a patient that involve the device are also disclosed.

42 Claims, 27 Drawing Sheets

U.S. PATENT DOCUMENTS

| | | | |
|---|---|---|---|
| 1,197,232 A | 9/1916 | Pierpont |
| 1,202,125 A | 10/1916 | Tullar |
| 2,217,575 A | 10/1940 | Hoff |
| 2,300,273 A | 10/1942 | Connell |
| 2,711,170 A | 6/1955 | Bornstein |
| 2,902,992 A | 9/1959 | Reenvall |
| 2,999,495 A | 9/1961 | Shipley |
| 3,046,978 A | 7/1962 | Lea |
| 3,461,866 A | 8/1969 | Ritchie |
| 3,473,529 A | 10/1969 | Wallace |
| 3,818,806 A | 6/1974 | Fumagalli |
| 3,890,967 A | 6/1975 | Elam et al. |
| 3,918,317 A | 11/1975 | Claussen |
| RE29,317 E | 7/1977 | Mosely et al. |
| 4,187,845 A | 2/1980 | Dror |
| 4,297,999 A | 11/1981 | Kitrell |
| 4,303,893 A | 12/1981 | Goldberg |
| 4,349,015 A | 9/1982 | Alferness |
| 4,430,893 A | 2/1984 | Barkalow |
| 4,501,271 A | 2/1985 | Clifton |
| 4,532,923 A | 8/1985 | Flynn |
| 4,591,271 A | 5/1986 | Byers |
| 4,898,166 A | 2/1990 | Rose et al. |
| 4,898,167 A | 2/1990 | Pierce et al. |
| 4,934,360 A | 6/1990 | Heilbron et al. |
| 5,305,739 A | 4/1994 | Gray |
| 5,313,938 A | 5/1994 | Garfield et al. |
| 5,345,929 A | 9/1994 | Jansson et al. |
| 5,628,305 A | 5/1997 | Melker |
| 5,645,056 A | 7/1997 | Pomeroy |
| 5,704,348 A | 1/1998 | Drews |
| 5,711,295 A | 1/1998 | Harris, II |
| 5,787,880 A | 8/1998 | Swanson et al. |
| 6,067,984 A | 5/2000 | Piper |
| 6,494,202 B2 | 12/2002 | Farmer |
| 6,792,947 B1 | 9/2004 | Bowden |
| 7,392,805 B2 | 7/2008 | Maguire |
| 2004/0173213 A1 | 9/2004 | Maguire |
| 2005/0056277 A1 | 3/2005 | Lurie et al. |
| 2005/0066976 A1 | 3/2005 | Wondka |
| 2006/0272644 A1 | 12/2006 | Halpern |

FOREIGN PATENT DOCUMENTS

| | | |
|---|---|---|
| WO | WO/2006/120404 | 11/2006 |

OTHER PUBLICATIONS

U.S. Appl. No. 11/952,094, filed Dec. 6, 2007, Halpern.

International Search Report for PCT/US07/86681 mailed Sep. 25, 2008.

International Search Report for PCT/US06/22011 (claiming priority to U.S. Appl. No. 11/147,070).

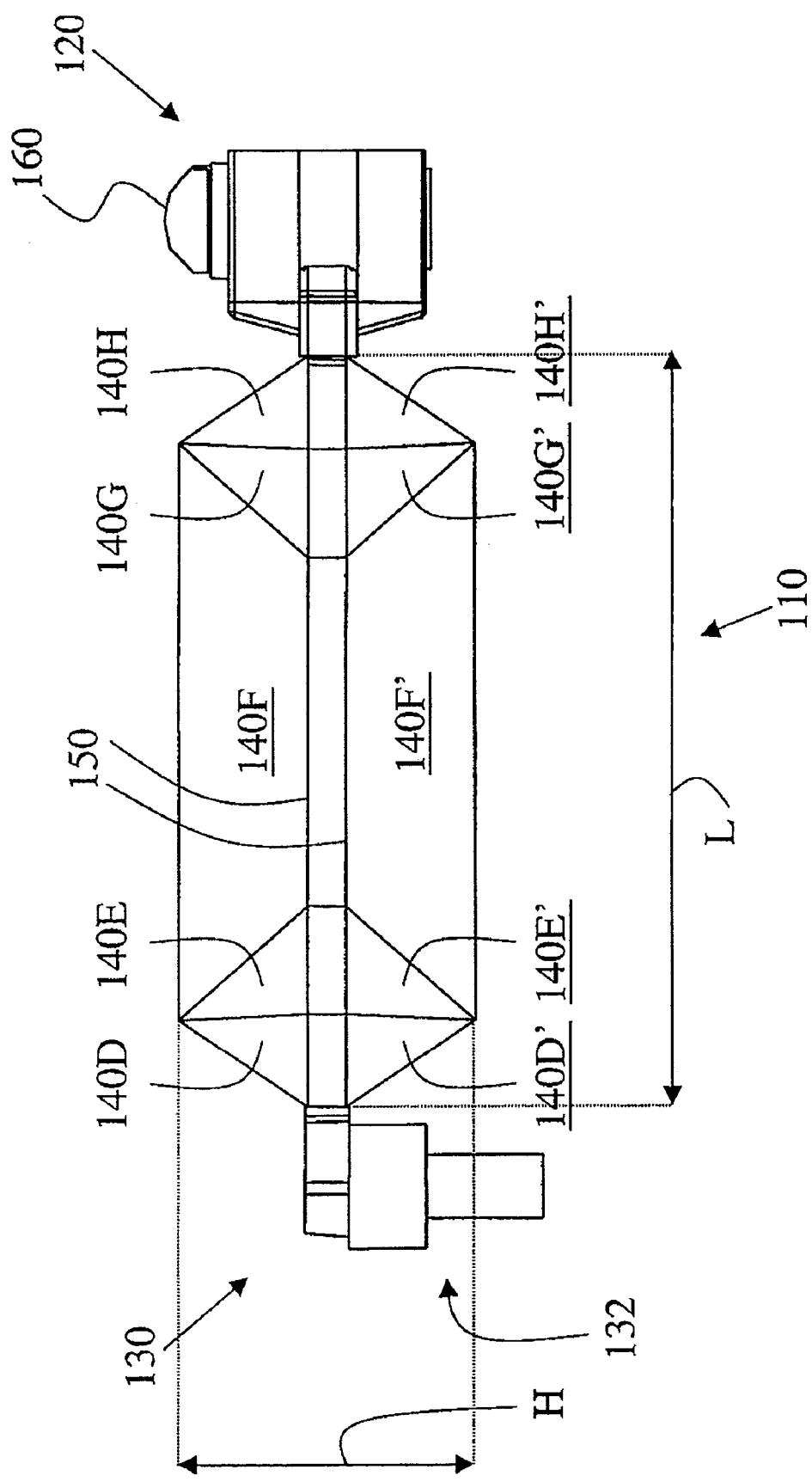
Figure 2 Side View

Figure 6  Exploded View

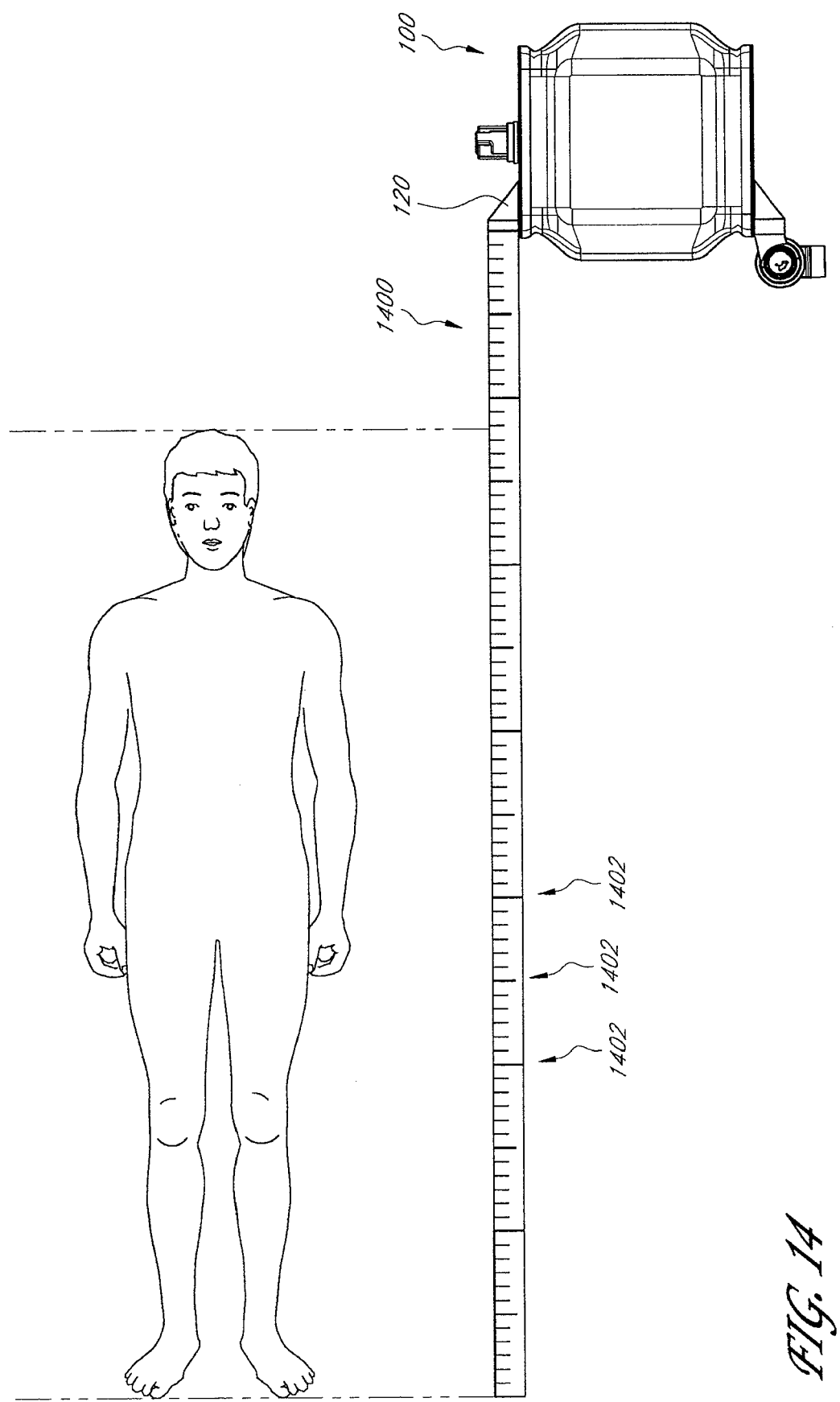

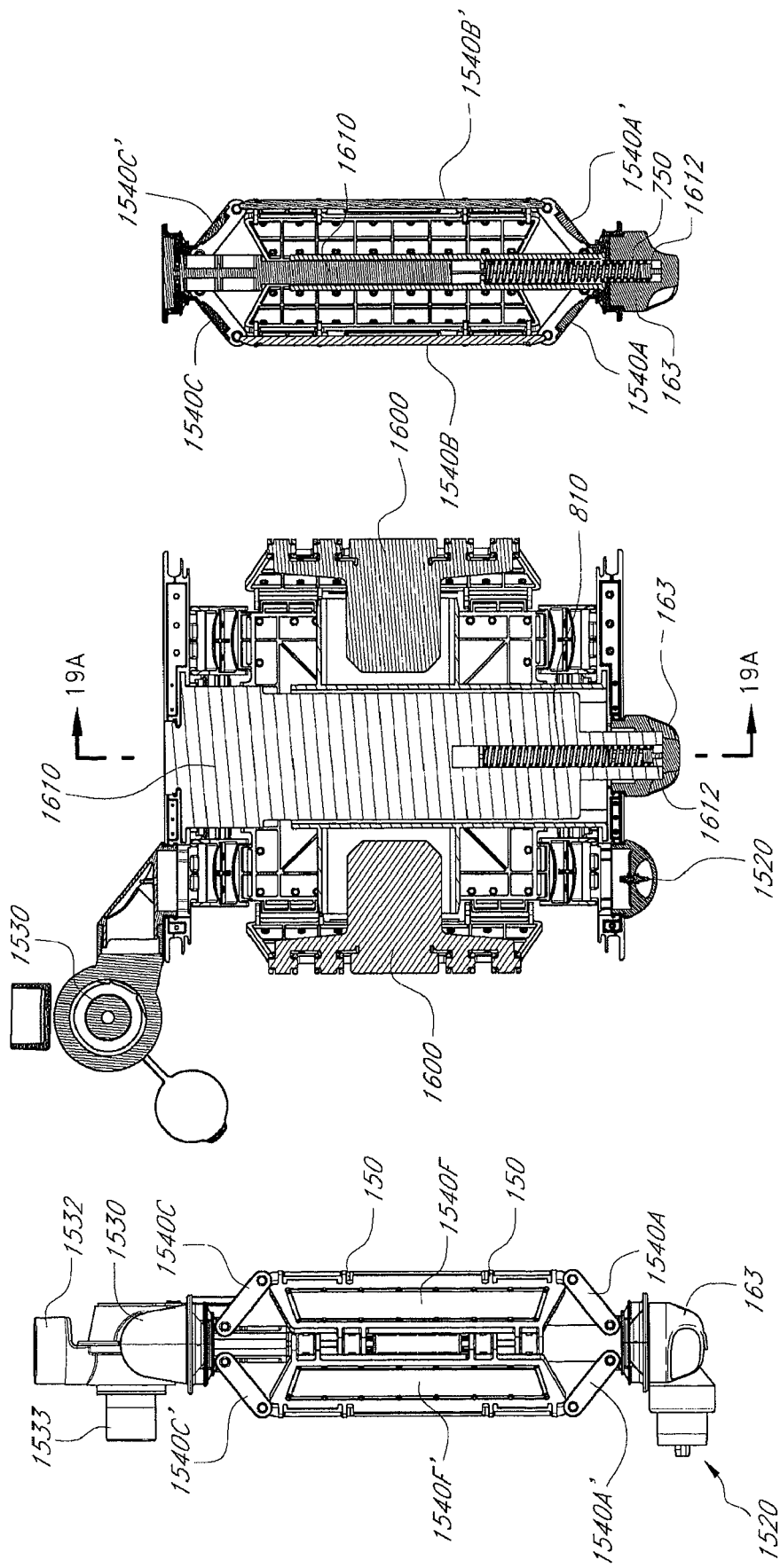

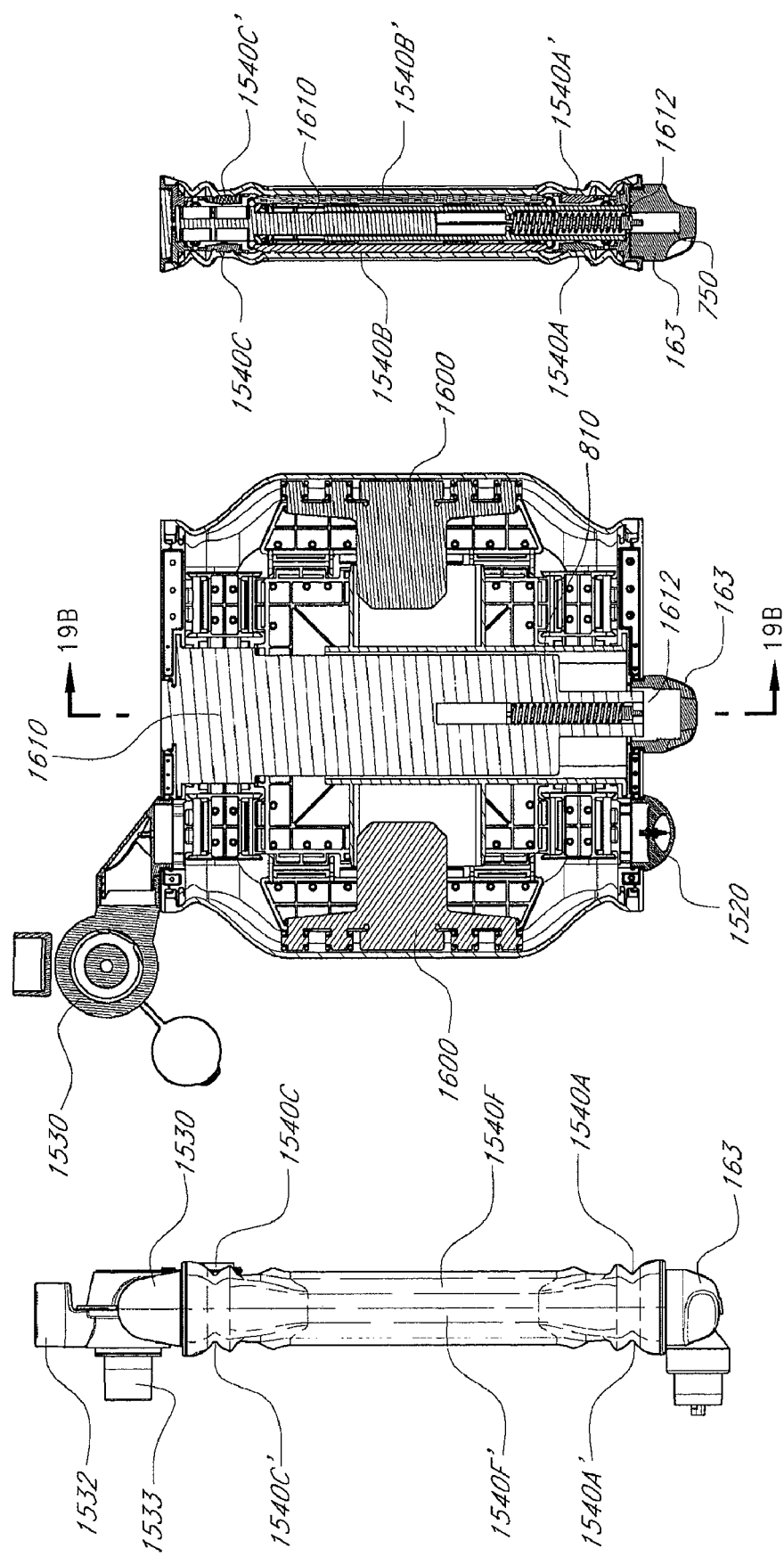

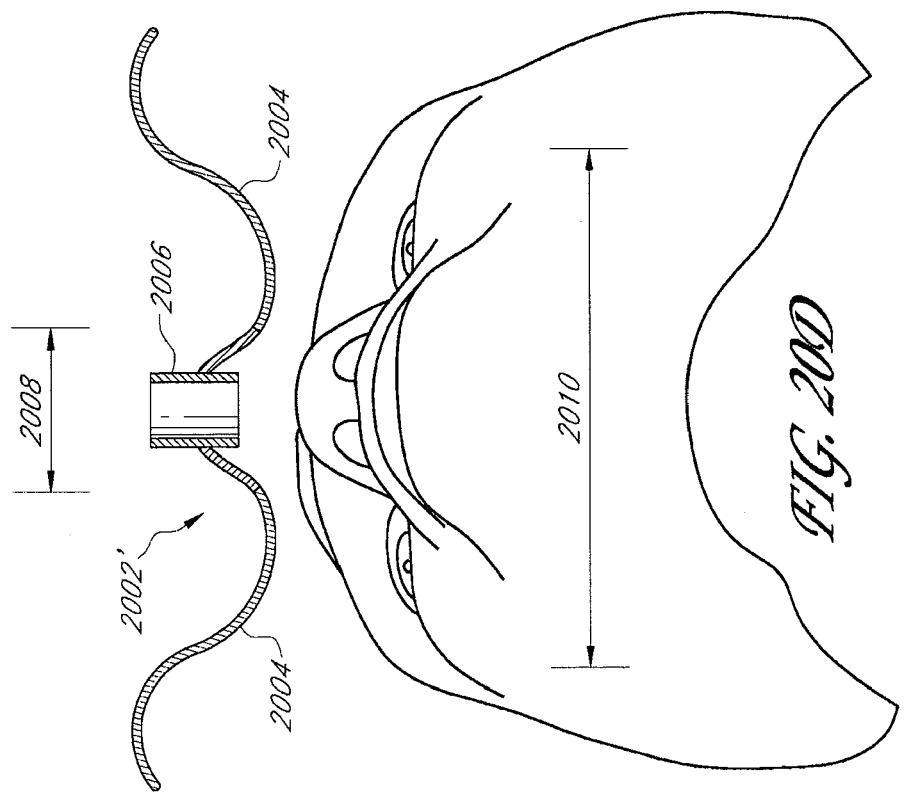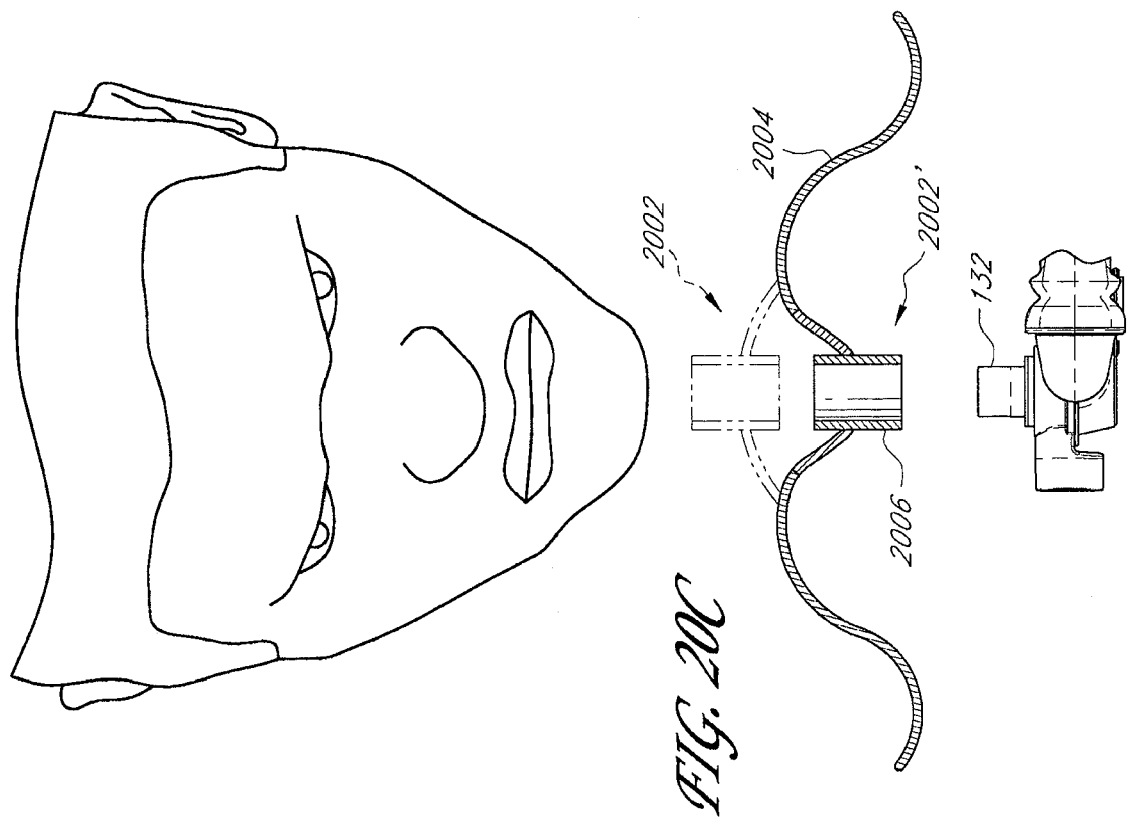

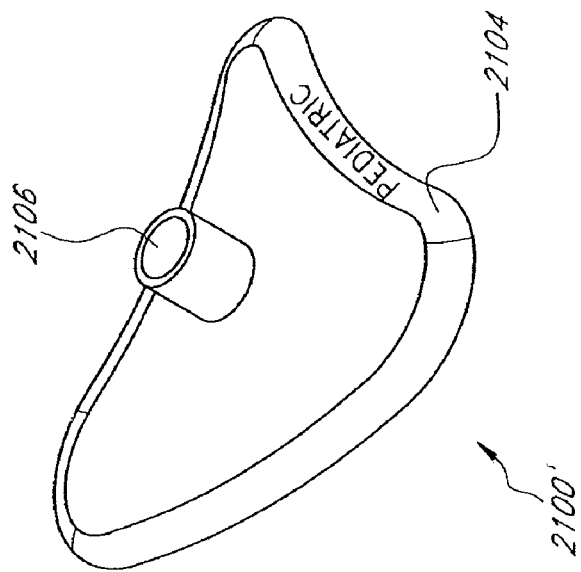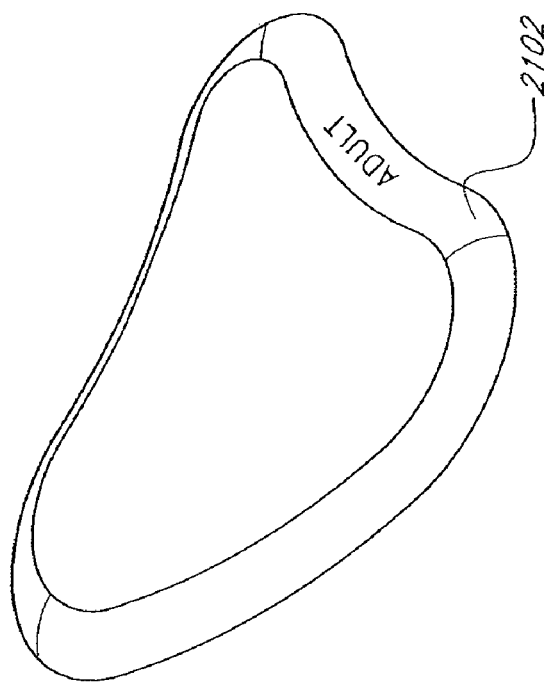
FIG. 21C

VOLUME-ADJUSTABLE MANUAL VENTILATION DEVICE

REFERENCE TO RELATED APPLICATIONS

This is a continuation-in-part application that claims the benefit under 35 U.S.C. §120 of U.S. patent application Ser. No. 11/147,070, filed Jun. 6, 2005 now U.S. Pat. No. 7,537,008, which is hereby incorporated by reference herein in its entirety.

FIELD OF THE INVENTION

The present invention relates generally to manual ventilation devices.

BACKGROUND OF THE INVENTION

Manual ventilation or resuscitation is performed on an individual when they are unable to breathe independently. Typically, this occurs when an individual is transported from one section of a hospital to another section such as an emergency room and an intensive care unit, or in an ambulance. Manual resuscitation also occurs during cardiopulmonary resuscitation (CPR), which is a standard technique applied to victims of cardiopulmonary arrest with the goal to re-establish normal cardiac and respiratory function.

Ventilation from a manual resuscitation device is currently provided by a self-filling elastomeric enclosure or bag. This bag is compressible by hand, a face-fitting mask (or intubation tube) in fluid communication with an outlet passage of the bag, and a one-way valve between the mask and bag to permit only fluid passage from the bag to the mask. The bag also has an inlet passage, typically with one opening for air and another, usually smaller opening for receiving oxygen. By squeezing the bag with their hand(s), a clinician delivers air or oxygen to an individual, and then releases the bag to permit it to expand to full size and thereby draw air or oxygen through the inlet passage.

The amount of air received by the lungs of the individual corresponds to the volume of the bag. A larger bag provides a greater maximum volume of air to be pumped into the individual. Children and infants typically have smaller lungs than an adult, and therefore conventional manual resuscitation devices are provided in different sizes; e.g., infant, child and adult. Each size provides a different maximum volumetric output of air. Depending on factors such as physical condition, body size, age, sex, etc., each individual may require a specific volume of air (tidal volume), and frequency, and minute ventilation.

Unfortunately, current manual ventilation or resuscitation devices are not suitable for the desired monitoring and control of tidal volume delivery. For instance, the collapsible bag portion of the resuscitation device allows the user to merely "feel" the amount of air they are providing to the individual. This provides them merely a very rough estimate of the volume of air they are providing and a tactile feel for when the lungs are non-compliant, i.e. are being pressurized. Although self-filling respiration (resuscitation) enclosures or bags can be selected on the basis of known maximum volumes, the volume actually delivered can vary substantially among several operators, dependent upon factors such as hand size, number of hands used, technique, enthusiasm and fatigue. These variations have been shown to be as much as 60 percent of the optimal tidal volume. Frequency can also vary between users, resulting in potential underventilation or overventilation.

Accordingly, what is needed is a single manual ventilation or resuscitation device that can be used on any patient, regardless of individual factors such as physical condition, body/lung size, age and sex.

SUMMARY OF THE INVENTION

In one aspect, disclosed is a ventilation device that includes a reservoir having a movable wall defining an enclosed volume, such that moving the wall expresses an adjustment limit. Moving the limit results in a change in the expressed maximum volume of the device.

In another aspect, disclosed is a single manual ventilation or resuscitation device. The body of the device has panels, that can be rigid, that encompass a sealed volume with an inlet mechanism and an outlet mechanism. The rigid panels are movable with respect to each other to allow the body to move between an uncompressed state and a compressed state. Once in compressed state a volume restoring mechanism is responsible to restore the volume from the compressed state back to the uncompressed state.

One of the objectives of the invention is to be able to hold the body with one hand and to compress the body with that one hand. To meet this objective, in one embodiment, the body is characterized by having a displacement in a direction of a hand displacement (e.g., height of the body) and at least one other direction (e.g., width of the body) other than this hand displacement. In another embodiment, the body is characterized by having a displacement in a direction of a hand displacement (e.g., height of the body) and at least two other directions (e.g., width and length of the body) other than this hand displacement. The displacement in width and/or length is a function of the height displacement and the geometry of the rigid panels.

The axial displacement of a panel is preferably no more than about 85 mm, preferably no more than about 20-25 mm, and more preferably no more than about 10-15 mm. Some of the displacements would have to comfortably fit between the thumb, one or more fingers and the web of the hand. In other words, the natural range of a grasping motion of a hand defines these displacements. The expressed (delivered) volume of the device, in some embodiments, can be no more than about 500 cc, or no more than about 250 cc (infant and child), or no more than about 1400 cc (infant to adult). In another embodiment, the expressed (delivered) volume of the device can range from about 250-1200 cc (child to adult).

A size adjuster is included to adjust one or more of the body displacements to change the dimension of the uncompressed state or volume. These axial size adjustments can be no more than about 170 mm, and preferably no more than about 25 mm in some embodiments. The objective of the size adjuster is to adjust the displacement to then adjust the volume of e.g., the air delivered to an individual. Hence the size adjuster is also referred to as a volume adjuster.

A frequency adjuster is included to adjust the time to restore the volume from the compressed state to the uncompressed state or to adjust the time to compress the volume from the uncompressed state to the compressed state.

Feedback mechanisms could be included to provide tactile feedback, visual and/or audible feedback to the user. An example of tactile feedback is to include tactile feedback areas, e.g., a flexible material, to cover an opening in a rigid panel. These areas allow the user to feel the compression force or lung resistance. These tactile areas are preferably sized and positioned to fit a thumb or one or more fingers of the user's hand. An example of a visual feedback mechanism is to provide the user feedback over the size (volume) adjustments or the frequency. An example of an audible feedback mechanism is to provide the user feedback over e.g., the compression speed, frequency, tidal volume, setting of the size (volume) adjuster or setting of the frequency control adjuster.

One advantage of the device is the ergonomic fit of the body to a user's hand in both uncompressed and compressed state, which reduces fatigue to hand and/or arm muscles. Another advantage of the device is the ability to adjust the volume and/or frequency so that the user can rely on a more or less constant tidal volume and tidal rate. Such ability allows one to use the device on any patient, regardless of individual factors such as physical condition, body/lung size, age and sex. Yet another advantage is that multiple devices could easily be stacked or nested with each other. In exemplary embodiments, the design and geometry could be configured to include such stacking or nesting capabilities.

In another aspect, disclosed is a manually operable volume-adjustable ventilation device. The device has a reservoir with an inlet mechanism, an outlet mechanism, and a volume adjuster configured to move a volume adjustment limit of the reservoir and change an expressed maximum volume of the reservoir. The reservoir has a body having a plurality of movable walls defining an enclosed volume. The reservoir has an uncompressed state and a compressed state. The walls of the reservoir are movable with respect to each other, such that moving the walls expresses the volume adjustment limit of the reservoir. The walls can be operably connected by movable structures configured such that two adjacent walls are configured to rotate around substantially orthogonal axes with respect to each other when the reservoir moves from an uncompressed to a compressed state. In some embodiments, the movable structures can be hinges, such as snap-fit assembly hinges. The movable structures and the movable walls can be co-molded together. In some aspects, the device can include a covering layer of the body of the reservoir. The covering layer can be a slide-on skin, and/or comolded or adhered to the walls of the reservoir.

In some embodiments, the device is configured such that applying a force to at least one of the walls of the device will result in the reservoir moving from the uncompressed state to a fully compressed state. The device can also be configured such that an expressed volume of the device for a given adjustment limit is consistently no more than about 10 cc of a disclosed volume setting on the volume adjuster from compression to compression for a given force of compression and airway resistance of a patient. The device can also further include a volume restoring mechanism to restore the reservoir from the compressed state to said uncompressed state. The volume restoring mechanism can be, for example, a compression spring, an extension spring, or a resilient covering layer. The volume adjuster can include a stop dial.

In some aspects, the device can further include a frequency adjuster to adjust the time to restore the reservoir from the compressed state to the uncompressed state, and/or the time to compress said reservoir from the uncompressed state to the compressed state. The device can be configured such that the maximum change in expressed volume of the reservoir is no more than about 1400 cc, no more than about 1200 cc, no more than about 500 cc, or no more than about 250 cc in some embodiments. The device can include tactile feedback areas on one or more of said walls. The tactile feedback areas can be flexible areas and sized and positioned to fit a thumb of a hand or one or more fingers of the hand. The device can also include a visual feedback mechanism. In some embodiments, the visual feedback mechanism is an expandable air reservoir operably connected to the inlet mechanism of the device; the air reservoir having an expandable wall configured to indicate the presence of air flow through the reservoir. In some embodiments, the device further includes an audible feedback mechanism, which is a pop-off valve in some embodiments.

The device can also include an air filter operably connected to the inlet of the device. Furthermore, the device can also include an inflow line with measurement markings to measure an aspect of the patient and estimate an appropriate expressed volume based on the measurement. In some aspects, the device can be compressed in a stored configuration to less than 35% of a fully expanded volume of the device; wherein the device is configured to deliver at least 95% of the fully expanded volume of the device after being stored for at least about 3 years, 5 years, 10 years, 15 years, or more. The device can also be configured such that three devices can be stacked in a shelf with a shelf height of no more than about 200 mm, or no more than about 180 mm. The device can also have a height of no more than about 70 mm and/or a side panel width of no more than about 50 mm to allow the device to be comfortably compressed in one hand by an operator.

In some aspects, also disclosed is a method of ventilating a patient. The method includes the step of providing a ventilation device that includes a reservoir with an inlet mechanism, an outlet mechanism, and a volume adjuster configured to move a volume adjustment limit of the reservoir and change an expressed maximum volume of the reservoir. The reservoir can include a body having a plurality of movable walls defining an enclosed volume. The reservoir has an uncompressed state and a compressed state. The walls can be movable with respect to each other, such that moving the walls expresses the volume adjustment limit of the reservoir. The walls can be operably connected by movable structures configured such that two adjacent walls are configured to rotate around substantially orthogonal axes with respect to each other when the reservoir moves from an uncompressed to a compressed state. The method also can include the step of selecting an appropriate expressed maximum volume setting from the volume adjuster. In some aspects, the device is connected the inlet of the device to an air or oxygen source. Also, the outlet of the device can be connected to a mask or tube configured to interface with a patient's airway. Next, the device can be actuated from an uncompressed state to a compressed state by applying a force to at least one wall of the device. In some aspects, the method includes the step of releasing the force to allow the reservoir to move back from the compressed state to the uncompressed state. The reservoir can moves back from the compressed state to the uncompressed state by the action of a volume restoring mechanism. As noted above, the volume restoring mechanism can be, for example, a compression spring, an extension spring, and a resilient covering layer. The movable structures can be hinges. The movable structures and the walls can be co-molded together. The device can be configured such that the maximum change in expressed volume of the reservoir is no more than about 1400 cc.

In some embodiments, selecting an appropriate expressed maximum volume setting from the volume adjuster involves turning a stop dial. In some aspects, the method includes the step of adjusting the time to restore the reservoir from the compressed state to the uncompressed state or adjusting the time to compress the reservoir from the uncompressed state to the compressed state. In some aspects, the method also includes the step of observing a visual feedback mechanism that indicates the presence of airflow into the device. The visual feedback mechanism can be, for example, an air reservoir with an expandable wall configured to indicate the presence of air flow through the reservoir. In other aspects, the method includes the step of listening to an audible feedback mechanism that provides feedback over one or more of the group consisting of: the compression speed, frequency, and expressed volume of the device. Also, the method can include the step of filtering air before air enters the body of the device.

Also disclosed is a face mask for use with a manually operable volume-adjustable ventilation device. The mask includes an inlet, an inner portion operably connected to the inlet, and an outer portion. The mask can be configured to transform from a first configuration to fit over an adult's face to a second configuration to fit over a child's face. The mask can also be configured to reversibly transform from a first configuration to fit over an adult's face to a second configuration to fit over a child's face. The inner portion can include a bi-stable cone movable between a first stable position to a second stable position. The mask can also include a tear-away seam between the inner portion and the outer portion.

In other embodiments, also disclosed is a face mask for use with a manually operable volume-adjustable ventilation device; the mask configured to create a sealing surface on a patient's face, the sealing surface extending substantially from cephalad at the base of the nose near the alar sidewalls to caudally under the mandible.

BRIEF DESCRIPTION OF THE DRAWINGS

FIG. 2 shows a side view of the device of FIG. 1, according to one embodiment of the invention.

FIG. 14 illustrates an inflow line configured to allow for measuring an aspect of the patient, according to one embodiment of the invention.

FIG. 17A is a side view of the ventilation device of FIG. 15 in an uncompressed state, with the covering layer removed for clarity.

FIG. 17B is a side view of the ventilation device of FIG. 15 in a compressed state.

FIGS. 18A-B are top horizontal sectional views of the ventilation device of FIG. 15 in uncompressed and compressed states, respectively.

FIG. 19A is a vertical sectional view of device 1500 through line 19A-19A of FIG. 18A.

FIG. 19B is a vertical sectional view of device 1500 through line 19B-19B of FIG. 18B.

FIGS. 20A-D illustrate a face mask that includes a bi-stable cone such that the mask can be reversibly transformed from a first configuration for adults to a second configuration for pediatric patients, according to one embodiment of the invention.

FIGS. 21A-C illustrate a face mask with a tear-away seam such that the mask can be transformed from a first configuration for adults to a second configuration for pediatric patients, according to one embodiment of the invention.

DETAILED DESCRIPTION OF THE PREFERRED EMBODIMENT

Although the following detailed description contains many specifics for the purposes of illustration, one of ordinary skill in the art will readily appreciate that many variations and alterations to the following exemplary details are within the scope of the invention. Accordingly, the following preferred embodiments of the invention are set forth without any loss of generality to, and without imposing limitations upon, the claimed invention.

Figure 1:
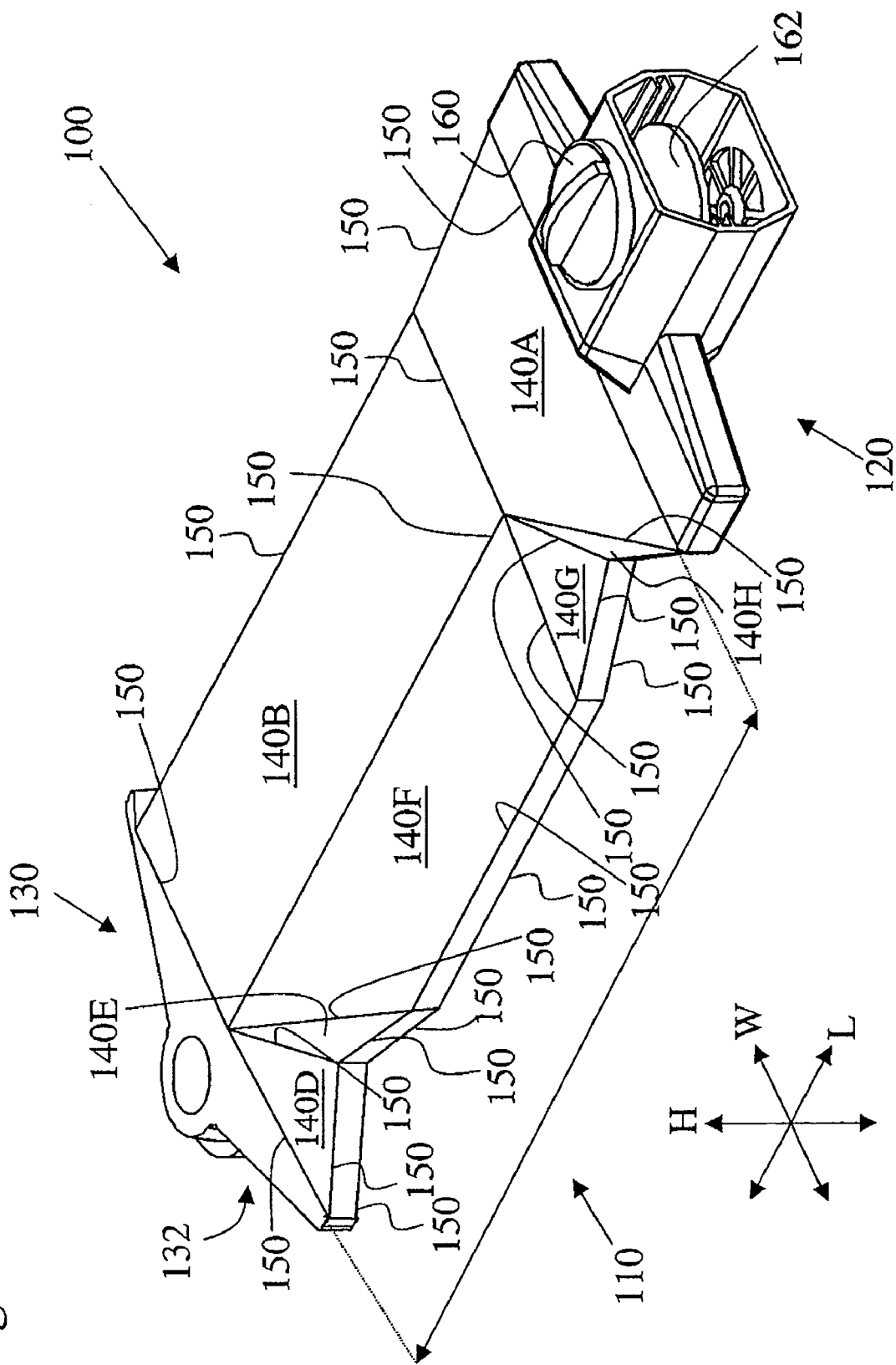
FIG. 1 shows a three-dimensional perspective view of a manual ventilation device, according to one embodiment of the invention.

A three-dimensional view of one example of the ventilation or resuscitation device 100 is shown in FIG. 1. In general, three parts can be distinguished: a reservoir that includes a body 110, an input mechanism 120 to allow input of e.g., air, oxygen, oxygen-enriched air, fluid, fluid mixture, gas, gas mixtures or any combination or derivative thereof in body 110, and an output mechanism 130 to output and deliver some or all of the inputted content from body 110 to an individual via connector 132. Body 110 distinguishes a plurality of movable walls (also referred to as panels herein). Movable walls can be, in some embodiments, panels that are movable with respect to each other. In some embodiments, the panels are rigid or substantially rigid. Design of body 110 with rigid panels encompasses a sealed volume that can contain e.g., air, oxygen or oxygen-enriched air. Another aspect of the invention is to be able to hold the body of the device with one hand and to compress the body with that one hand. In one embodiment, as will be clear from reading the description, disclosed is a device with a body having rigid panels whereby the body is characterized as having a displacement in a direction of a hand displacement and at least one other direction other than that particular hand displacement.

In the particular example of FIG. 1 body 110 distinguishes a plurality of panels; e.g., panels forming the top, panels forming the bottom, and panels for each side. More particularly, the following (main) panels can be distinguished, i.e. panels 140A, 140B, 140D, 140E, 140F, 140G and 140H, which are all visible in FIG. 1; panels 140D, 140E, 140F, 140G, 140H, 140D', 140E', 140F', 140G', 140H', which are all visible in FIG. 2; panels 140A, 140B, 140C, 140D, 140E, 140F, 140G, 140H, 140D", 140E", 140F", 140G" and 140H", which are all visible in FIG. 3; and panels 140C and 140C', which are all visible in FIG. 4. Panels blocked from the views in FIGS. 1-4, are 140A', 140B', 140D''', 140E''', 140F''', 140G''', 140H'''. The relative positions and orientations of the panels blocked in the figures is readily appreciated by a person of ordinary skill in the art to which this invention pertains.

Figure 4:
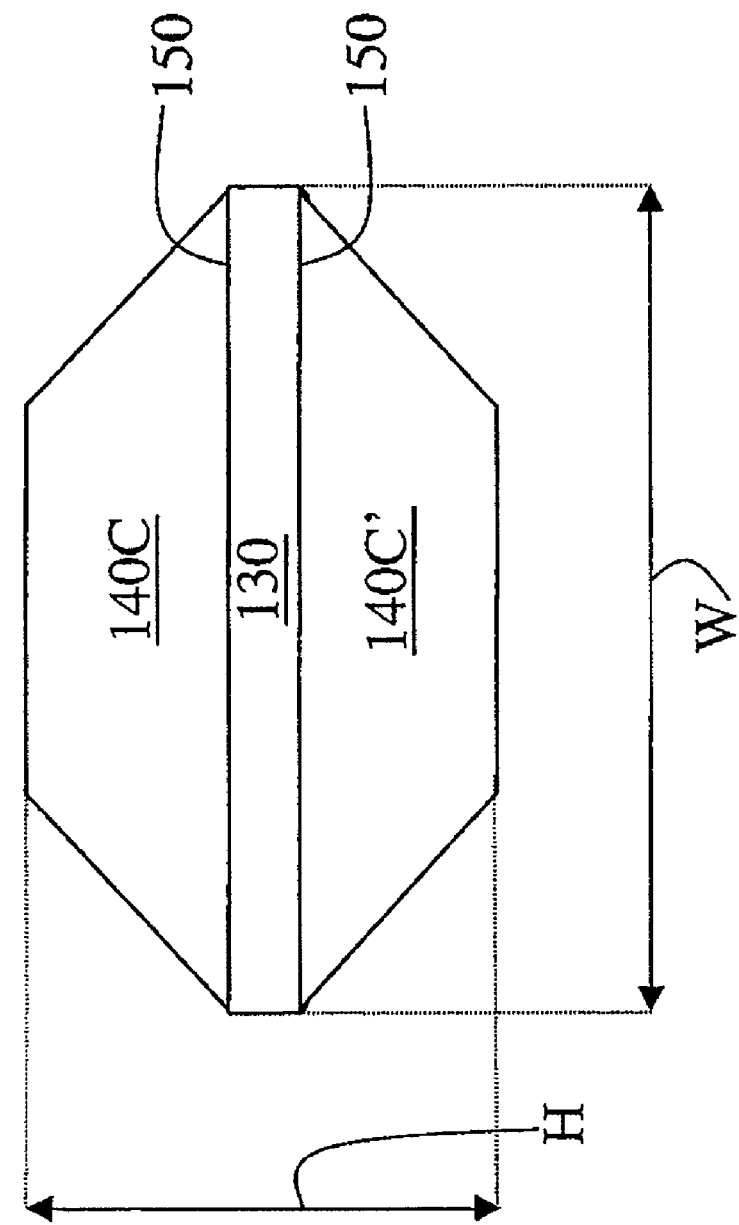
FIG. 4 shows a front view of the body of the device of FIG. 1, according to one embodiment of the invention. The hook-up to a mask or intubation tube, and outlet is left out for clarity.

The movable parts or structures, indicated by 150 in FIGS. 1, 2 and 4 could be living joints/hinges, snaps, joints, fabricated flexures, heat-shrinked joints or flexures, welded joints, simple mechanical hinges, pinned hinges, flexible hinges, snap-fit assembly hinges, or the like. The type of movable structure 150 depends on the type of manufacturing that is used to create the rigid panels and body. Examples of different types of manufacturing of the panels, movable structures and body are e.g., blow molding, heat sealing, overmolding, the mechanical assembly of a rigid paneled chassis with a flexible bladder or skin to form the body, coining to form living hinges, assembly using gaskets as seals in hinges, injection molding, ultrasonic welding, radio frequency welding, dielectric welding, high frequency welding, dipping, extrusion, spray coating, brush on, assembly of adhesive backed sheets of various materials, and/or any type of manufacturing that results in a body with rigid panels that are movable with respect to each other. In some embodiments, the panels of the body 110 and the movable structures 150 are co-molded together to allow for the use of a very compliant low durometer material for the panels of the device 100 to advantageously provide a soft grip for an operator of the device, while still utilizing a very durable, rigid material for the movable structures 150. A person of ordinary skill in the art to which this invention pertains would readily appreciate the different types of manufacturing that can be used to make body 110, which are known techniques in the mechanical and design engineering art. Input mechanism 120 and output mechanism 130 could be manufactured and integrated along with the manufacturing process of body 110 or later assembled to body 110. The types of materials that can be used for the rigid panels, input mechanism 120, output mechanism 130 and other structures of the device are, for example, polymers, plastic, polyethylene, polycarbonate, high impact polystyrene, K-resin, ABS, PVC, acetal, polypropylene, silicone, thermoplastic elastomers, thermoplastic rubbers, latex, fabrics, cardboard, or the like.

The volume delivery is preferably consistent from compression to compression, as well as consistent with respect to a disclosed volume setting on the volume adjuster. In a preferred embodiment, the device 100 is configured to output a consistent, reproducible volume for a given speed of compression of the device 100 by an operator and for a given airway resistance. In some embodiments, the actual volume delivered differs by no more than about 50 cc, 40 cc, 30 cc, 25 cc, 20 cc, 15 cc, 10 cc, 5 cc, or less than the volume selected on the volume adjuster to be delivered. In some embodiments, the device 100 can be configured such that the actual volume delivered per compression can be consistently reproducible within no more than about 50 cc, 40 cc, 30 cc, 25 cc, 20 cc, 15 cc, 10 cc, 5 cc, or less from a preset delivered value (e.g., from volume adjuster) compression to compression.

The device 100 is also preferably configured to preferably deliver a consistent volume regardless of the manner or speed in which the device is compressed. In some embodiments, the device 100 is configured to deliver a consistent volume when compressed using a mechanical force, for example, one hand, two hands, one foot, two feet, a knee, in between two knees, an elbow, or a forearm (while bracing the device against a thigh or other surface, e.g., a table or the patient's head). The device 100 is also preferably configured such that applying a force to any one or more of the walls of the body 110 will result in delivery of a consistent volume, and will also result in the device achieving a fully compressed state. The fully compressed state of the device 100 preferably has a volume of no more than about 40%, 35%, 30%, 25%, 20%, 15%, 10% or less of the uncompressed state of the device 100.

Body 110 has an uncompressed state where the panels are positioned to create a volume that can be filled with e.g., air, oxygen or oxygen-enriched air. From the uncompressed state, body 110 can change to a compressed state where the panels are moved with respect to each other to decrease the volume with respect to the volume in the uncompressed state. In other words, moving the rigid panels with respect to each other from the uncompressed state to the compressed state, air, oxygen or oxygen-enriched air is outputted via output mechanism 130. The uncompressed state could be at full expansion (i.e. maximum volume) or any intermediate state (See also size adjuster (volume) description). Restoring the volume allows entry of new air, oxygen or oxygen-enriched air into the volume via input mechanism 120.

In some embodiments, the device 100 also includes an air filter. The air filter is preferably integrated with the device, for example, via an adapter operably connected to the input mechanism 120. The air filter can advantageously remove dust, pollen, mold, bacteria, viruses, and other airborne particles from an air source prior to entry into body 110 of the device 100. In some embodiments, the air filter is configured to meet or exceed HEPA (high efficiency particulate air) filter standards.

Body 110 has a height H, width W and length L (see FIGS. 1-4). In general, the state changes of body 110 could be characterized by the height H of body 110 being larger in the uncompressed state compared to the compressed state. The height changes cause changes in width W and length L, which are smaller in the uncompressed state compared to the compressed state. The width and length changes are a function of the height changes and the geometry of panels as a person of ordinary skill would readily appreciate. It is further noted that the body could be characterized by having at least two of the panels capable of rotating around substantially orthogonal axes with respect to each other; consider e.g., panels 140F and 140C which are both involved in the height changes, but given their orientation, 140F is further related to the width changes, and 140C is further related to the length changes. In summary, the body is characterized as having a displacement in a direction of a "hand displacement (e.g., height of body) and at least two other directions (e.g., width and length of body) other than the particular hand displacement (e.g., height of body).

Figure 1A:
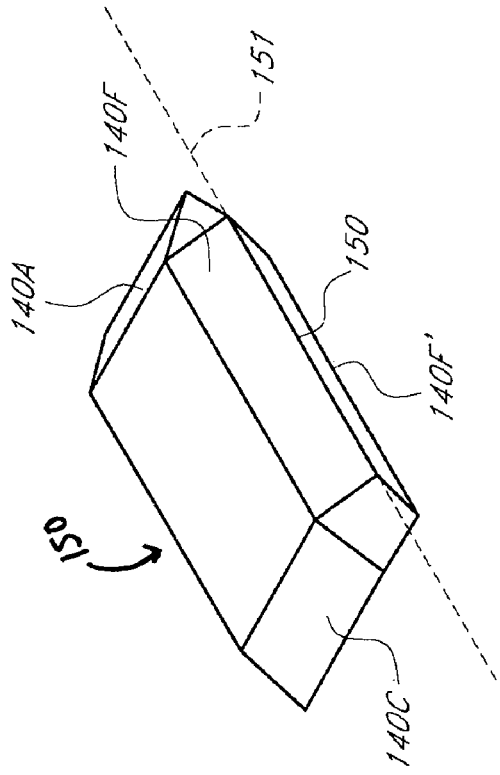
FIGS. 1A-C are schematic diagrams illustrating movement of panels of a manual ventilation device in the presence and absence of movable structures, according to one embodiment of the invention.
Figure 1B:
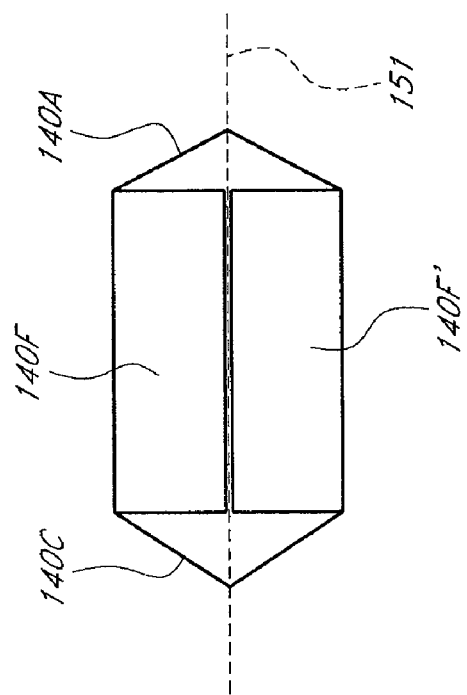
Figure 1C:
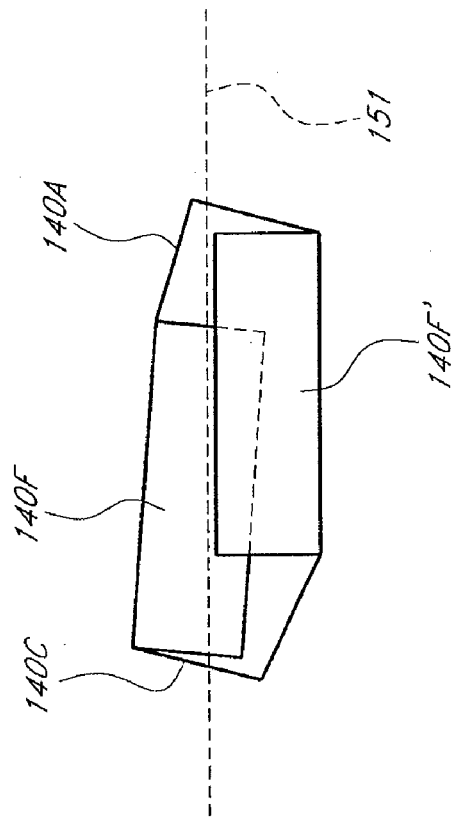
Figure 3:
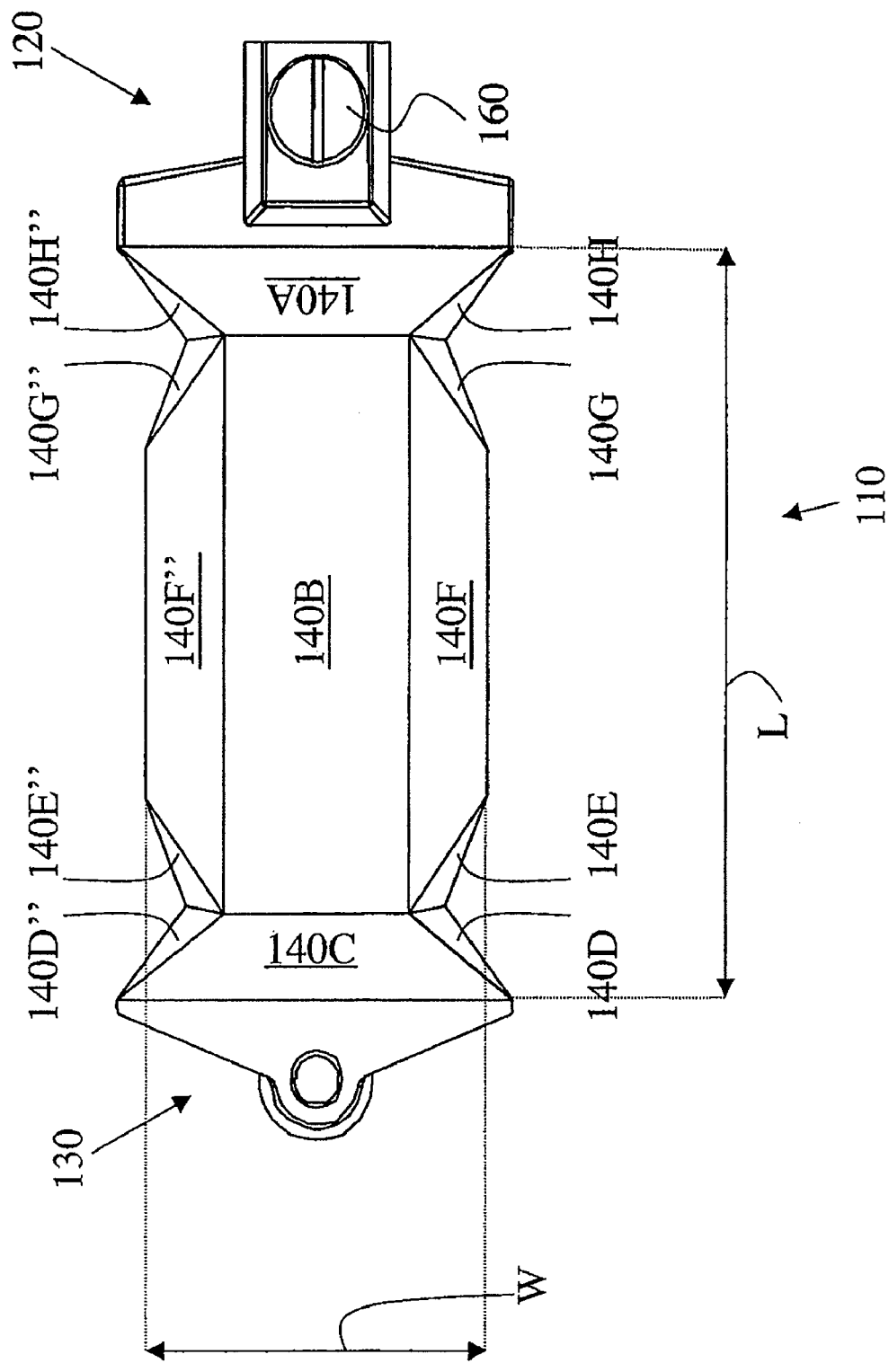
FIG. 3 shows a top view of the device of FIG. 1, according to one embodiment of the present invention.

FIGS. 1A-1C are schematic diagrams illustrating the interaction of panels 140 where movable structures 150 are either present or absent on a ventilation device 100. FIG. 1A shows that adjacent movable walls (e.g., 140F and 140F'; 140F" and 140F''' are not shown) can be operably connected by movable structures 150, which can be snap-fit assembly hinges, according to one embodiment of the invention. Dotted line 151 represents an axis, defined by the border between two adjacent walls 140F, 140F' as shown, around which walls 140F and 140F' can rotate with respect to hinge 150. The movable structures 150 are preferably configured such that a movable structure 150 operably connected to two adjacent walls can rotate substantially uniformly around the axis 151 when the reservoir 110 of device 100 moves from an uncompressed to a compressed state, and vice versa. In this way, the hinges 150 operably connected to adjacent walls, e.g., 140F, 140F' advantageously provide for generally uniform collapse and expansion of the device 100 substantially preventing non-uniform bending or sliding of the walls 140F, 140F' in axes other than axis 151 as shown; preventing non-uniform bending of walls 140A and 140C as shown, and resulting in consistent volume delivery to a patient. This is in contrast to a ventilation device that collapses non-uniformly due to the absence of stabilizing movable structures (such as hinges 150) between, for example, unhinged folds of inflatable bladders, disclosed, for example in U.S. Pat. No. 4,898,167 to Pierce et al., which is hereby incorporated by reference in its entirety. The absence of stabilizing movable structures (such as hinges 150) can result in rotation and/or flexing of the folds in multiple axes, and consequently, inconsistent volume delivery. The side view schematics shown in FIGS. 1B-1C illustrate how device 100 would non-uniformly rotate without hinges 150 operably connected to panels 140F and 140F'. FIG. 1B is a side view schematic of the device of FIG. 1A depicting panels 140A, 140C, 140F, 140F' without hinges 150. FIG. 1C is of the same side view as FIG. 1B after compression of the device. As shown, the absence of movable structures between, for example, panels 140F and 140F' can allow panels to rotate non-uniformly in multiple axes other than 151. End panel 140A, for example, could rotate non-uniformly with respect to panel 140C. As noted above, this can undesirably lead to inconsistent volume delivery.

The body could also have a higher or a smaller number of panels than body 110, as a person of average skill in the art to which this invention pertains would appreciate. For example, the panels could be assembled radially around central top and bottom panels and more panels can be added, for example, 140F can be broken up into two or more panels. An example of reducing panel numbers could be achieved by reducing 140A, 140B and 140C to only two panels. In the latter example the body would have height and width or length changes. In summary, such bodies could be characterized as having a displacement in a direction of a hand displacement (e.g., the height of body) and at least one other direction (e.g., the width or length of body) other than the particular hand displacement (e.g., the height of body).

As mentioned above, one of the key objectives of the invention is to be able to hold the device with one hand and to be able to compress the body with that one hand. To meet the objective the height and width changes in uncompressed and compressed state are therefore constrained since they would need to fit: (i) the hand of a user and (ii) the grasping (or squeezing) range of motion of the user.

Furthermore, the thumb and one or more fingers are desirably positioned on body 110 to create a mechanical advantage (i.e. a large moment arm with respect to the point of rotation) when compressing the body. Such a mechanical advantage meets another objective of the invention, which is to reduce fatigue of the hand muscles and potentially also the arm muscles.

Figure 5:
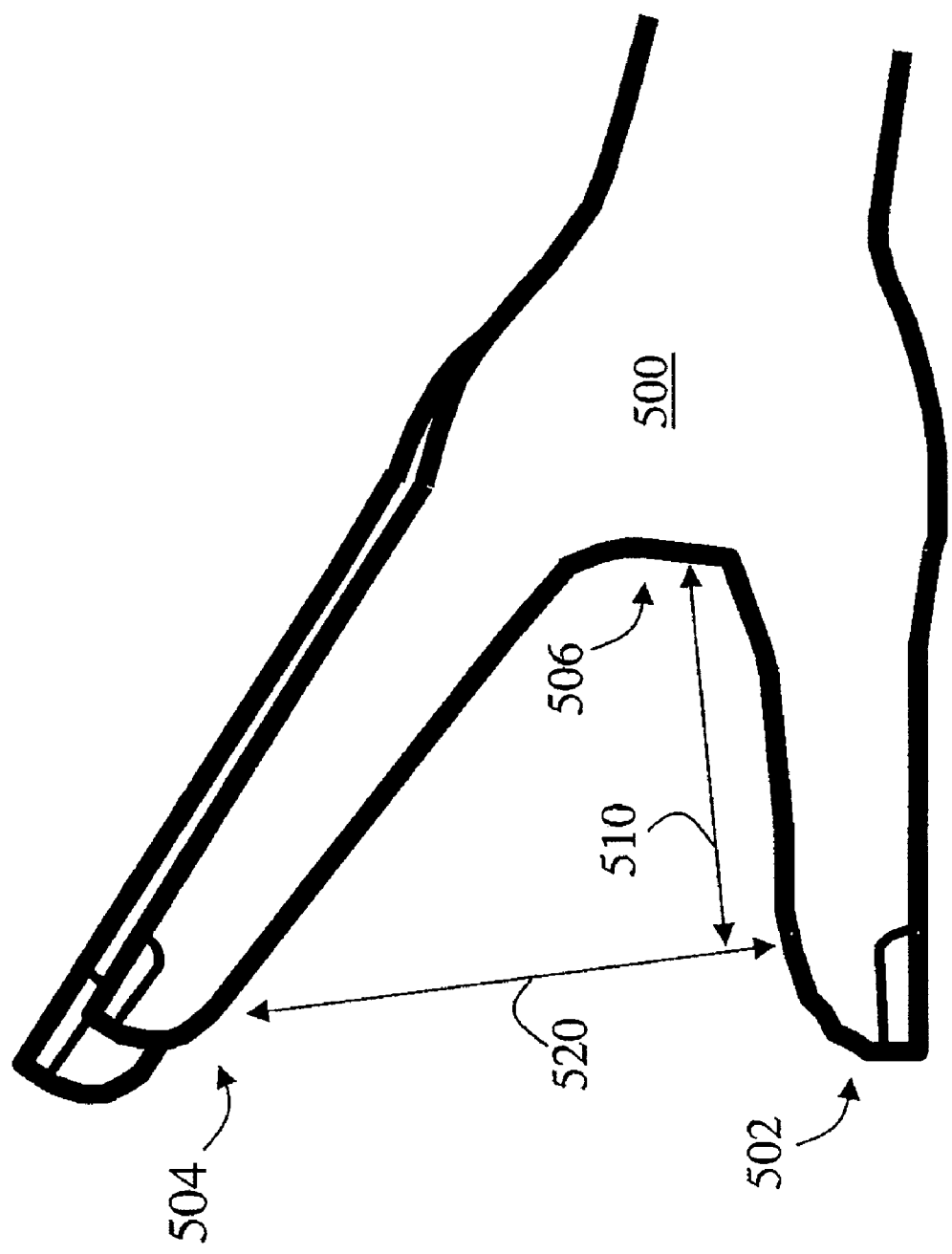
FIG. 5 shows a hand with dimensions for grasping and operating the device according to one embodiment of the invention.

FIG. 5 shows hand 500 with thumb 502, one or more fingers 504 and web of the hand 506 between which body 110 is typically held. Given a variety of hand sizes (e.g. male, female, large and small) in mind one could determine a reasonable range of motion and a comfortable fit to the user's hand that constrains the height and width dimensions of body no when moving between the uncompressed state and a compressed state. The maximum height of the fully expanded device, in some embodiments is no more than about 100 mm, preferably between about 45-70 mm with a side panel (e.g., panels other than 140B and 140B' in some embodiments) width of no more than about 60 mm, preferably between about 30-50 mm. These dimensions, for example, advantageously allow the device to be compressed in one hand comfortably by a wide range of both male and female operators of the device 100. In some embodiments, the height and width (displacement) changes of a single panel axially could be no more than about 85 mm, preferably no more than about 20-25 mm and more preferably no more than about 10-15 mm. The height changes would correspond to a hand displacement 520 in FIG. 5 and the width changes would correspond to a hand displacement 510 in FIG. 5. A person of average skill in the art to which this invention pertains would readily appreciate that the geometry (dimensions and relative angles) of the panels could be varied to meet the desired height and width (displacement) changes as well as the desired deliverable tidal volume.

The length changes of a single panel axially could also be no more than about 85 mm but is, in some embodiments, not constrained by hand dimensions, but will be a variable in determining the change in volume. The change in enclosed volume of the device (in other words, the deliverable or expressed volume of a device) is typically no more than about 1400 cc in some embodiments. In other embodiments, the deliverable volume ranges from about 250 to 1200 cc, which covers tidal volume ranges for children and adults. When the device is used for infant or child purposes the volume changes are smaller and preferably are no more than about 500 cc. The maximum deliverable volume of a device can, in some embodiments, be adjusted in increments of at least about 25 cc, 50 cc, 75 cc, 100 cc, 125 cc, 150 cc, 200 cc, or more. The ability to configure the device to set an adjustable maximum deliverable tidal volume advantageously provides an increased level of safety and reduces the risk of excess volume delivery, and thus complications of volutrauma such as pneumothorax.

Figure 6:
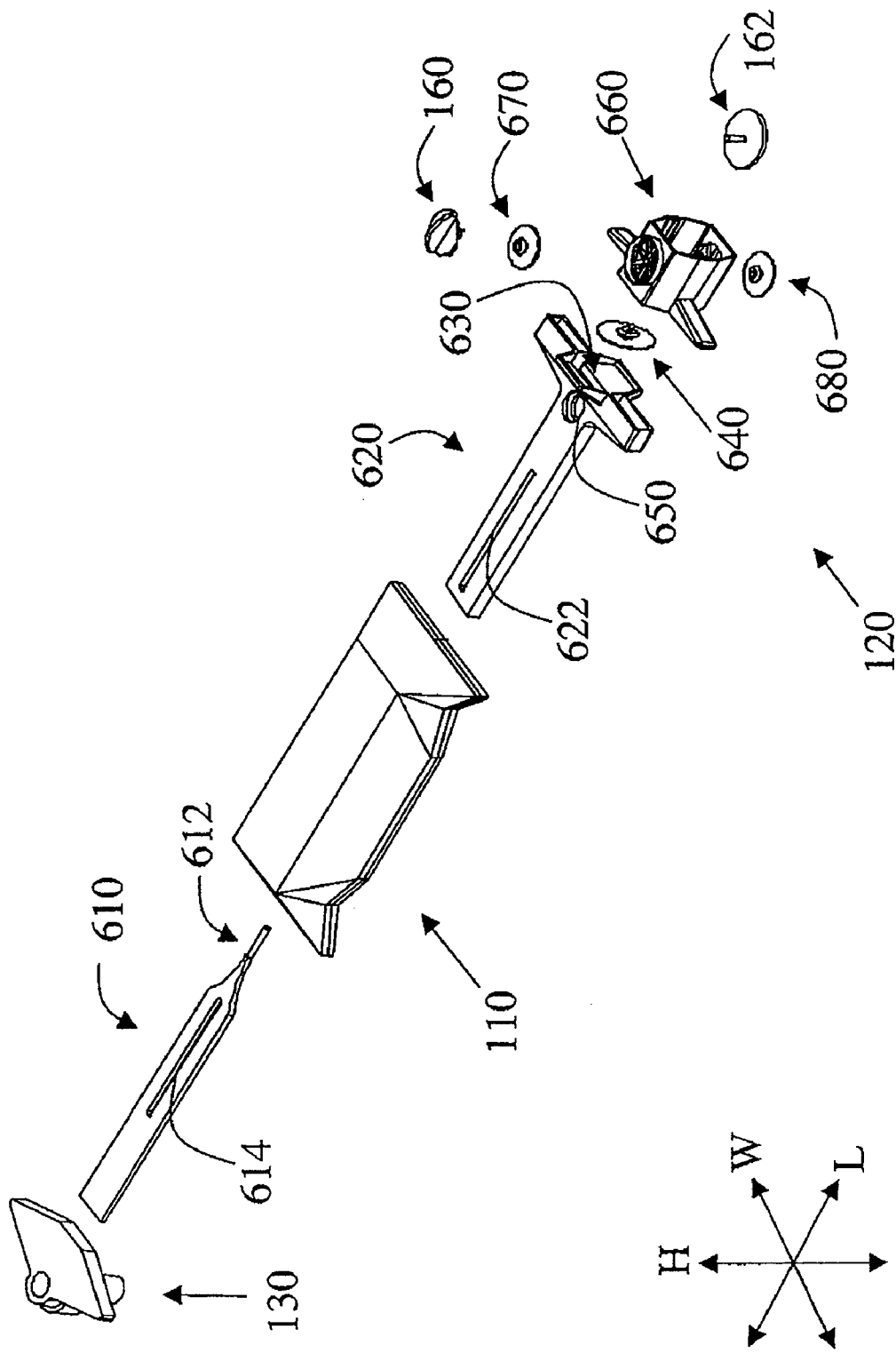
FIG. 6 shows an exploded view of the device of FIG. 1, according to one embodiment of the invention.

FIG. 6 shows an exploded view of an embodiment of a ventilation device. In addition to the elements discussed above, the device further includes a main shaft 610 connected to output mechanism 130 and positioned inside body 110. Main shaft 610 has narrow (cylindrical) end 612 and a slot 614. The device further has a receiving shaft 620 connected (or could be a single part) to input mechanism 630 and also positioned inside body 110. Receiving shaft 620 has an opening (not visible in figure) sized to allow travel of main shaft 610 along the length of receiving shaft 620. It further has a slot 622 preferably of equal size as slot 614; slots 614 and 622 should also be aligned with each other as will be understood when discussing volume recovery from compressed state to uncompressed state with respect to FIG. 8. Opening 630 could be sized such that element 660 could be mechanically assembled by ultrasonic welding, snap fit, press fit, adhesive or any other known techniques in the mechanical and design engineering art. Element 660 allows fitting and attachment of air/oxygen input devices. A flutter valve 640 is fitted to the front opening of element 660 allowing e.g. air travel into receiving shaft 620 through opening 650 and then into body 110. Element 660 further houses a size adjuster (also referred to as volume adjuster).

In general, the size adjuster of the device adjusts the length changes, width changes and/or height changes. The size adjuster serves the purpose of easily adjusting the deliverable volume so that the user can rely of a fairly constant volume of deliverable e.g. air, oxygen or oxygen-enriched air. Adjusting the deliverable volume is important to compensate for factors such as physical condition, body size, age, sex, etc.

In a preferred embodiment, size adjuster is integrated with input mechanism 120, in particular with element 660, and adjusts the travel length of body 110. The size adjuster distinguishes an adjustment knob 160 placed on top of element 660 and conveniently accessible to a user. The adjustment knob 160 is connected to an adjustment dial 162, which in this example is positioned inside element 660; the connection could e.g. be through either valve 670 or 680.

Figure 7:
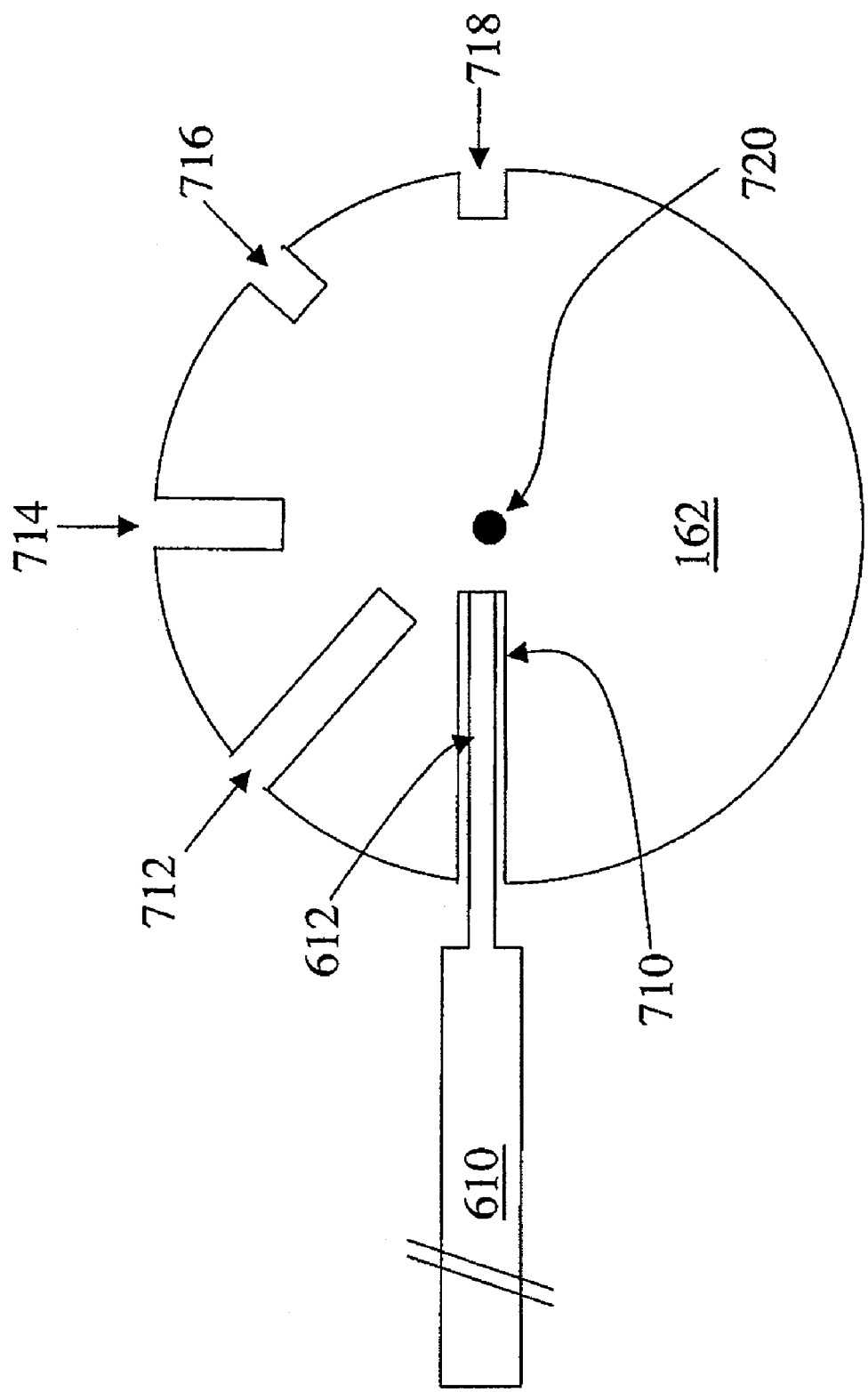
FIG. 7 shows an example of a size (volume) adjuster of the device according to one embodiment of the invention.

FIG. 7 shows adjustment dial 162 with a number of slots 710, 712, 714, 716 and 718. These slots are sized to fit narrow (cylindrical) end 612 of main shaft 610 that is able to travel all the way through the opening of receiving shaft 620 (as well as through flutter valve 640; not shown in figure) when moving between uncompressed and compressed states. By changing adjustment knob 160, adjustment dial 162 is rotated around pivot 720 to a new slot position; this is typically done when the body is in compressed state. It is noted that size adjuster changes the dimension of the uncompressed state or volume.

Slots restrict the travel distance of main shaft 610 and therewith control the deliverable volume to an individual. Slot sizes could be up to no more than about 170 mm to allow changes in length, and preferably are no more than about 25 mm. The number of slots and the sizes of the slots are selected to cover a reasonable range of deliverable tidal volumes as a person of ordinary skill in the art will appreciate.

In the example of FIG. 7, the size (length) (volume) adjuster is placed outside body 110. A person of average skill in the art to which this invention pertains would appreciate that the size adjuster can also be positioned inside the body or intrinsic to the design of the body. Furthermore, the size adjuster could also be added for width or height control or any combination of height, length or width, or any other direction in a similar fashion as shown in FIG. 7.

Figure 7A:
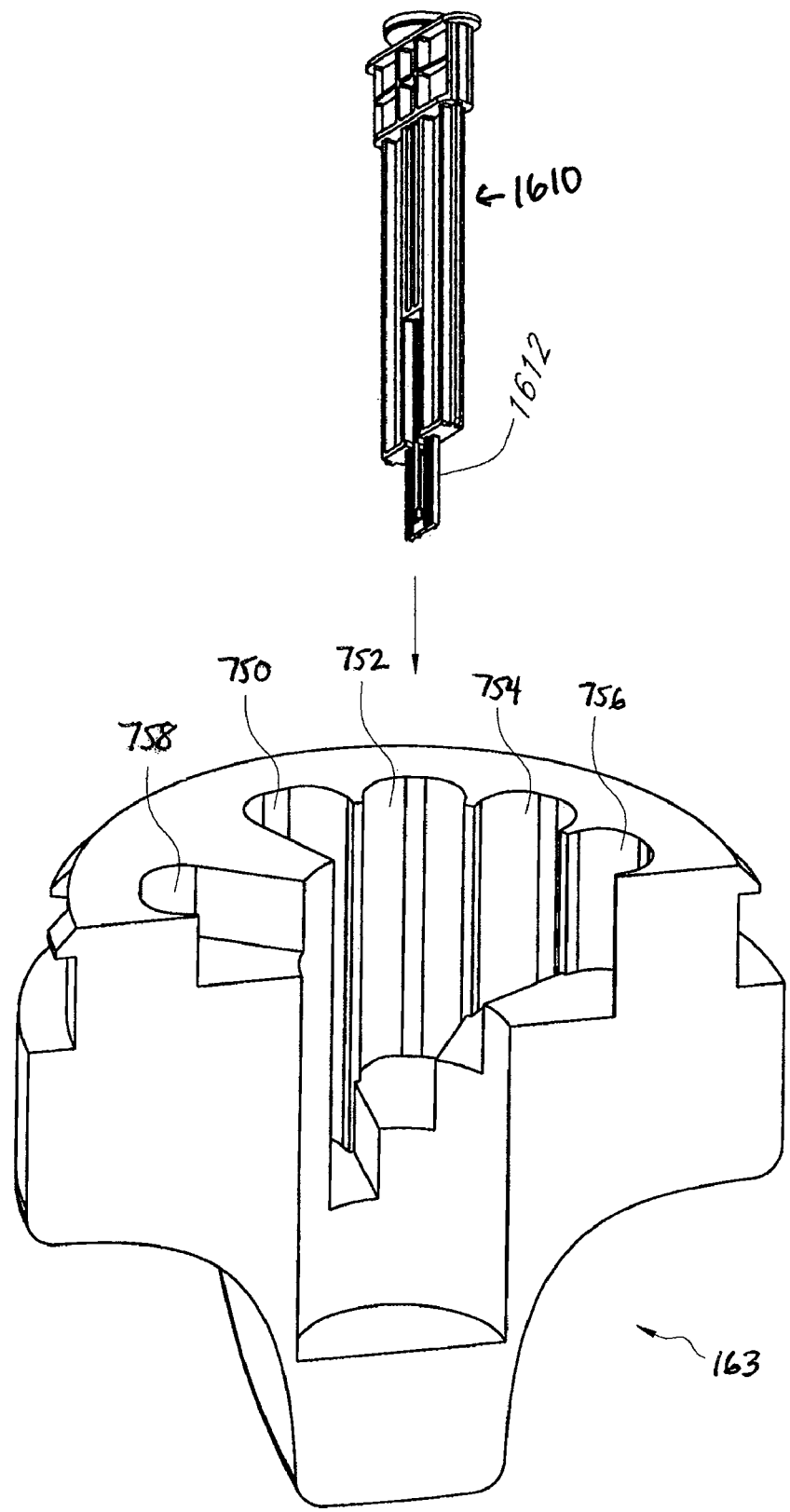
FIG. 7A illustrates an exploded perspective cut-away view of an adjustment dial, according to one embodiment of the invention.
Figure 7B:
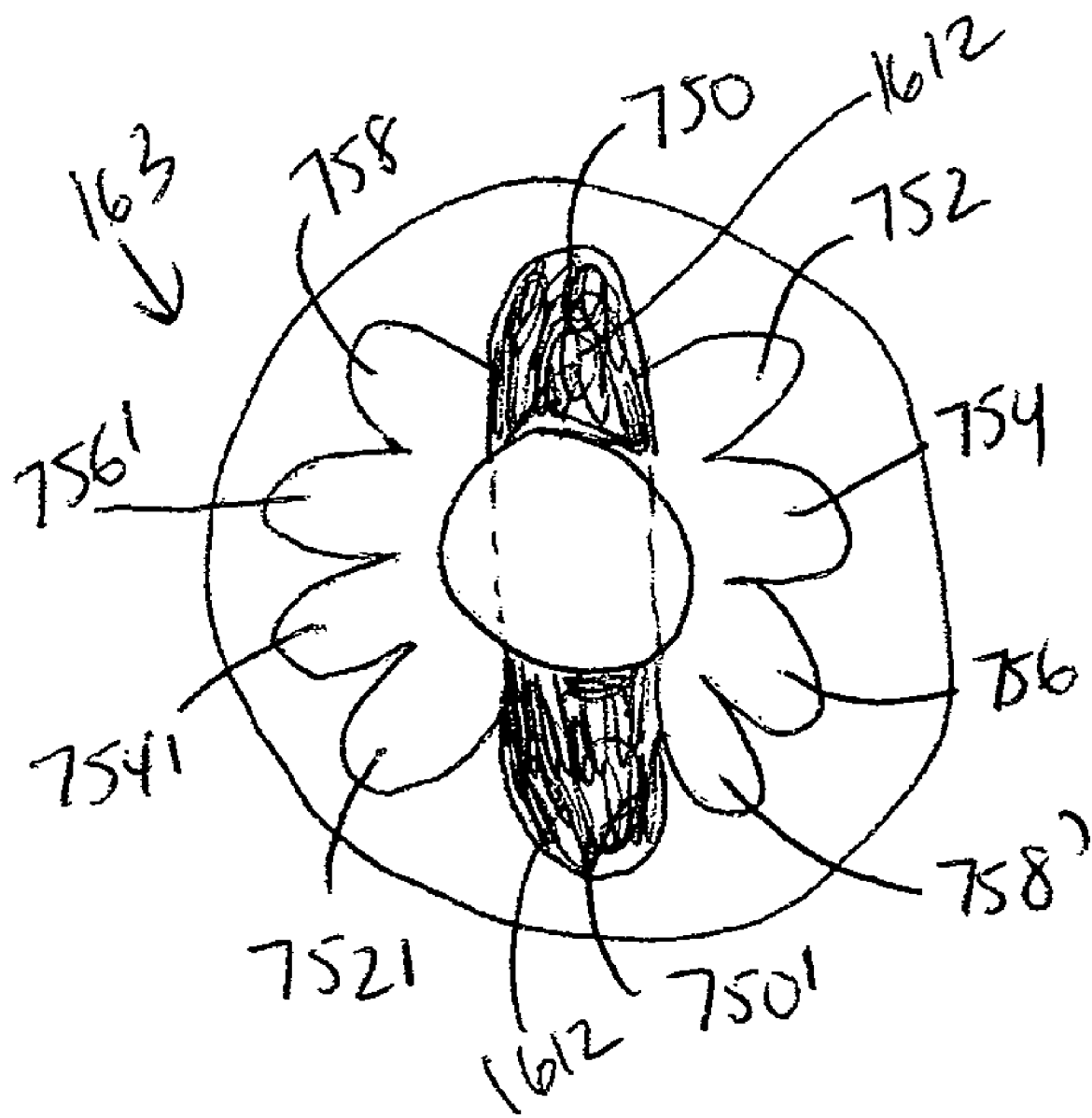
FIG. 7B illustrates a horizontal sectional view of an adjustment dial, according to one embodiment of the invention.

FIG. 7A illustrates an exploded perspective cut-away view of another adjustment dial 163, according to one embodiment of the invention. Shown are the variable-length slots 750, 752, 754, 756, 758 that are configured to fit the narrow end 1612 of a slider-type volume adjuster, such as 1610 of FIG. 16 (shown in FIG. 7A not necessarily to scale). Narrow end 1612 can be rectangular, although other shapes can also be used as known in the art. Turning the adjustment dial 162 in an appropriate direction will thus change the travel distance of main shaft of slider 1610 within the body 110 of device 100, and thus control the tidal volume delivered to an individual as noted above. In some embodiments, the slots 750, 752, 754, 756, 758 are configured such that turning the adjustment dial 163 to allow end 1612 of slider 1610 to engage an adjacent slot will produce a change in deliverable tidal volume of at least about 25 cc, 50 cc, 75 cc, 100 cc, 125 cc, 150 cc, 200 cc, or more. In some embodiments, a label (not shown) is present on or near adjustment dial 163 to assist an operator by indicating, for example, the numerical tidal volume correlating to the appropriate slot, and/or whether the slot setting is appropriate for adults, children, or infants. FIG. 7B is a horizontal sectional view of an adjustment dial 163 with slots 750, 750', 752, 752', 754, 754', 756, 756', 758, 758' in which slots spaced 180 degrees apart, such as slots 750, 750' have the same or substantially the same length to accommodate end 1612 of slider 1610.

Instead of a size adjuster with slots, one could design and integrate different types of mechanisms, which are all within the scope of the present invention. Examples of such variations are e.g. an adjustable threaded stop for the main shaft, an element with chambers whereby each chamber has grooves or each chamber has different depths, a slotted tube with different positions of the slots to set travel constraints to the main shaft, deflecting stops that deflect when adjusted in an incorrect or uncompressed state, a rack and pinion system with stops, ratcheting band (adjustable zip-tie), adjustable cam, a rotating dial of spring loaded stops that deflect when adjusted in an incorrect or uncompressed state, or any type of engineering mechanism that constrains the travel of the main shaft to control the volume output.

Figure 8:
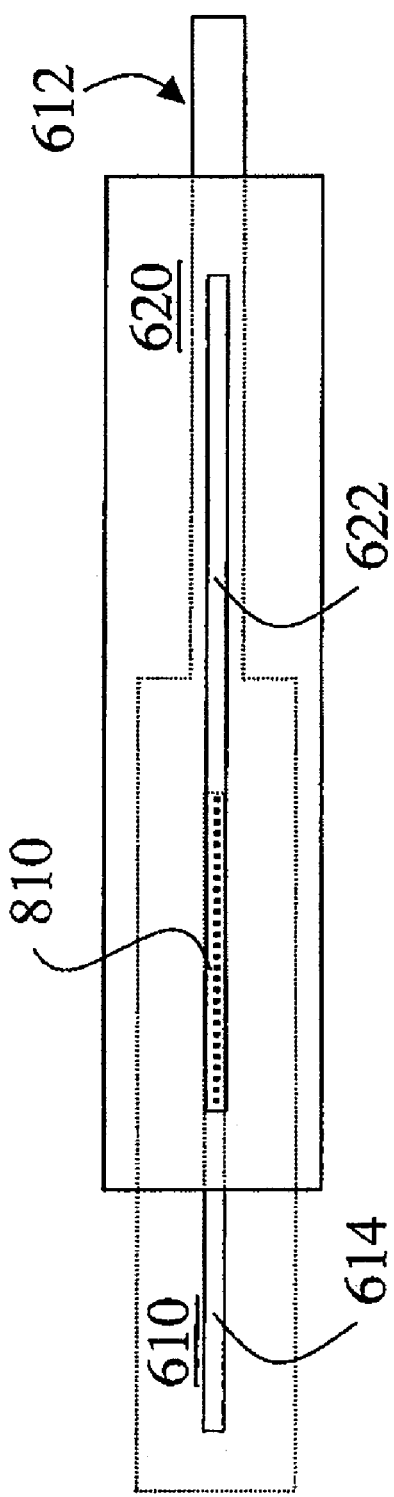
FIG. 8 shows an example of a mechanism to restore the volume of the body of the device from a compressed state to an uncompressed state according to some embodiments of the invention.

FIG. 8 shows an example of a volume restoring mechanism to restore the volume from a compressed state back to the uncompressed state. This could be accomplished by main shaft 610 traveling inside receiving shaft 620 whereby (part of) slots 614 and 622 travel inline with each other. One site of slot 614 is connected to an opposite site of slot 622 by element 810, which is e.g. an extension spring, plastic or rubber. When we change from uncompressed state to compressed state, force is built-up in element 810. This force is then used to restore the body back to the uncompressed state when the user releases the compression force applied to body 110. As a person of average skill in the art to which this invention pertains would appreciate, the volume restoring mechanism could also be outside body 110 or intrinsic to body 110 (e.g. one could have the restoring force as an intrinsic property of the movable joints 150). Other alternatives are a leaf spring mechanism inside body 110 that builds up force when compressed or an extension spring/mechanism placed inside body 110 but not integrated with the two shafts. The volume restoring mechanism could be adjusted using similar techniques as discussed for the size (volume) adjuster or it could be left to one setting.

In an alternate embodiment, the device includes a frequency adjuster to set and control the time to: (i) restore the volume from a compressed state back to the uncompressed state, and/or (ii) compress the volume from uncompressed state to a compressed state. The volume restoring mechanism as discussed above could be used as a frequency adjuster/controller. However, in this scenario, the frequency control is then still in hand of the user and not constrained by the device. Control over frequency is desired to enforce consistency in tidal volume rate. Therefore in another embodiment a frequency adjuster is added in a similar fashion as the size adjuster.

A frequency control knob could be placed at the opposite site of element 660 and implemented to adjust the frequency by e.g. a rack and pinion mechanism in combination with the main shaft to set the dampening of travel of the main shaft, a rack and pinion mechanism coupled with rotationally resistant gears, a polymer escapement mechanism, a friction brake, a rotationally resistant ratchet wheel, or a track to deflect the travel of the main shaft. All such mechanisms, which are known in the mechanical and design engineering art, can be adjusted via a frequency control knob to change the dampening of the travel of the main shaft, whereby an increase in dampening would result in a decrease in frequency. Similarly to the size adjuster mechanism, the frequency adjuster could also be inside the body, outside the body or intrinsic to body.

Figure 9:
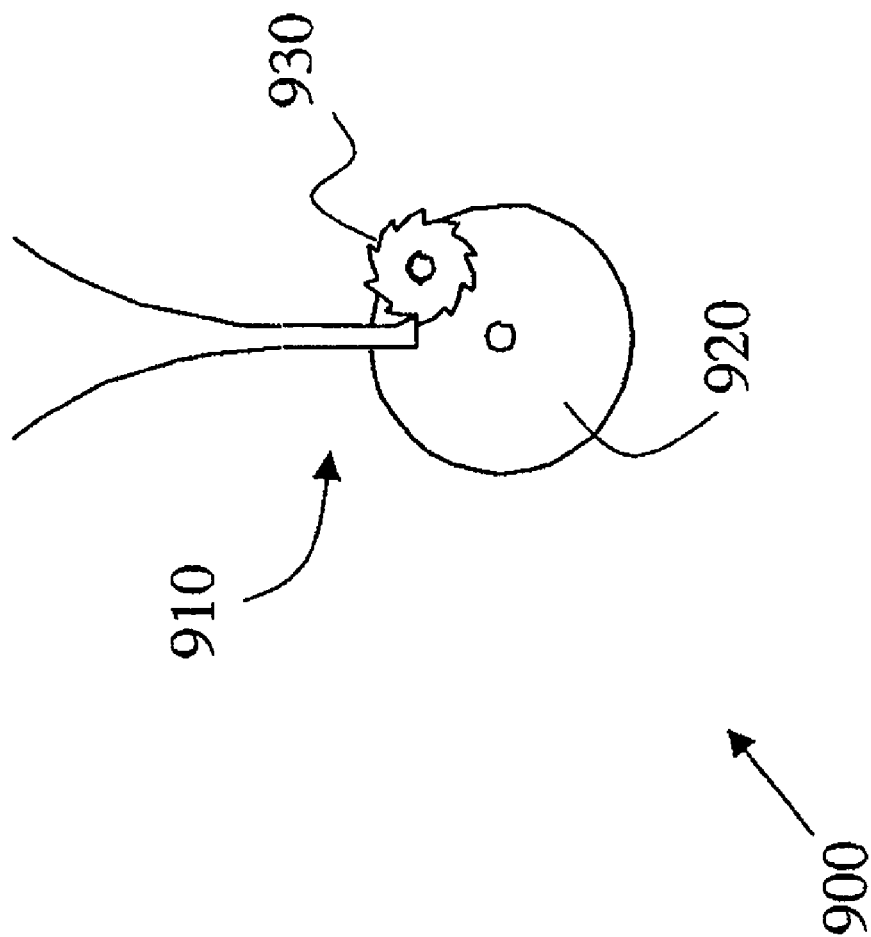
FIG. 9 shows an example of a frequency adjuster of the device according to one embodiment of the present invention.

FIG. 9 shows an example of an embodiment of a frequency control mechanism 900 that is accomplished by a ratchet mechanism 910 placed on frequency control knob 920. Frequency control knob 920 can extend up from an identical knob to volume control knob 610, inverted and assembled to the bottom of the element 660. A ratchet wheel 930 can be assembled to frequency control knob 920 by e.g. a snap fit, a fastener or any other means. Frequency control knob 920 can be rotated with ratchet wheel 930 in line with the main rod's travel or outside of its travel. The ratchet wheel's rotation can be dampened by multiple methods such as e.g. a friction insert, a roll pin, a coil or a watch spring, a high friction disc, or the like. There could be a variety of ratchet wheels along the circumference of frequency control knob 920 to adjust the resistance to main rod 610 depending on the rotation direction of frequency control knob 920. In some embodiments, the frequency control mechanism 900 can be configured such that the device can deliver no more than about 40 breaths per minute. In some embodiments, frequency control mechanism 900 can be configured to adjust frequency in increments of no more than about 10, 8, 6, 5, 4, 3, 2, or 1 breaths per minute.

Figure 10:
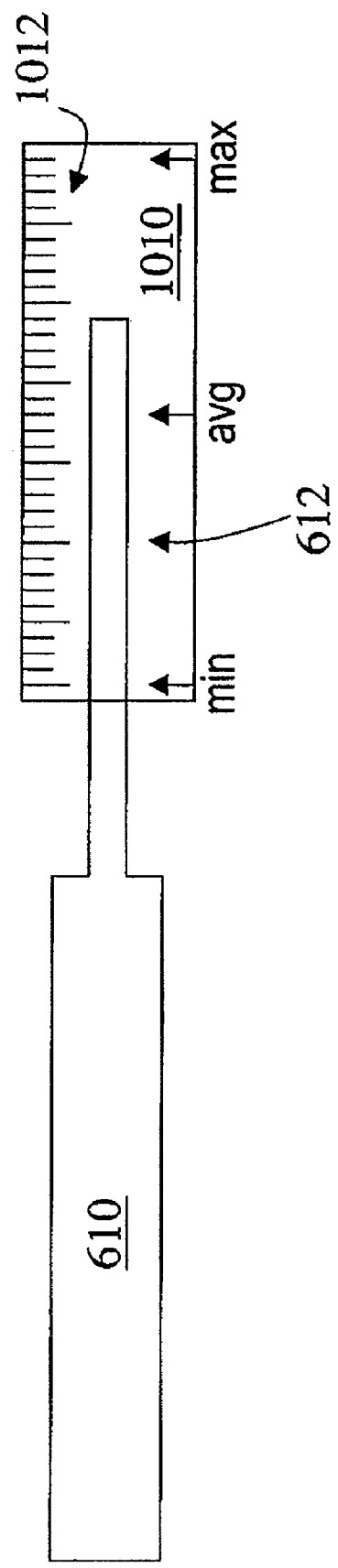
FIG. 10 shows an example of a visual feedback mechanism according to one embodiment of the present invention.

A visual feedback mechanism could be added to provide the user with visual feedback (colors, markings, symbols, or the like) on the adjustments to size, travel of the main shaft, or the frequency. FIG. 10 shows an example of a visual feedback mechanism for the size (volume) adjustments. Main shaft 610 could travel across a ruler 1010 designed to indicate e.g. minimum min, average avg, and maximum max deliverable tidal volume (expressed volume). The relative position of narrow end 612 of main shaft 610 to markings 1012 could further assist in fine-tuning the desired volume. The visual feedback mechanism could be placed inside a body whereby the body has a transparent part allowing a user to visualize the visual feedback mechanism. A similar feedback mechanism could be applied for the frequency.

One could further add an audible feedback mechanism (beeps, timers, commands, warnings, or the like) that provides feedback over the compression speed, frequency, tidal volume, setting of the size (volume) adjuster or setting of the frequency control adjuster. Another example is to have a click mechanism associated with the travel of the shaft(s) and/or changes in volume. The clicking sounds could also be used as a tactile feedback; e.g. the clicks can be felt through the hand. In some embodiments, the audible feedback mechanism is a pop-off valve that can be operably connected to output mechanism 130. The pop-off valve can be configured to provide an audible cue when a certain threshold airway resistance is reached, thus alerting the operator of the device of a potential airway problem such as a foreign body, pneumothorax, or inadvertent gastric intubation.

Figure 11:
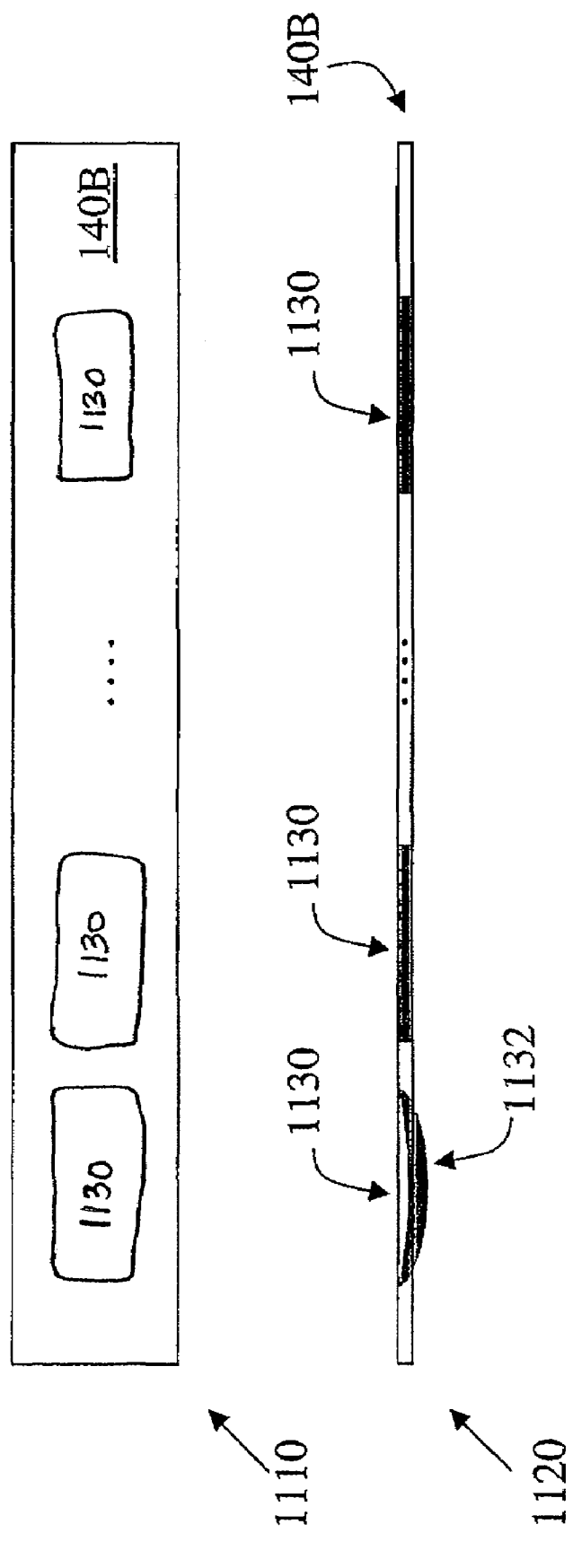
FIG. 11 shows an example of a tactile feedback mechanism according to one embodiment of the present invention.

In still another embodiment, one could add tactile feedback areas 1130 on one or more of panels such as panel 140B as shown in FIG. 11; 1110 is a top view and 1120 is a side view. Tactile feedback areas 1130 are sized and positioned to fit a thumb of a hand or one or more fingers (e.g., on panel 140B') of the hand. These areas are made of a flexible material that is responsive to thumb or finger pressure as well as pressure from e.g. the air/oxygen inside the body. This will provide the user additional feedback on the compression force and lung resistance. Deflection 1132 of flexible material 1130 with respect to the rigid panel 140B illustrates the deflection caused by e.g. a finger during compression.

Figure 12:
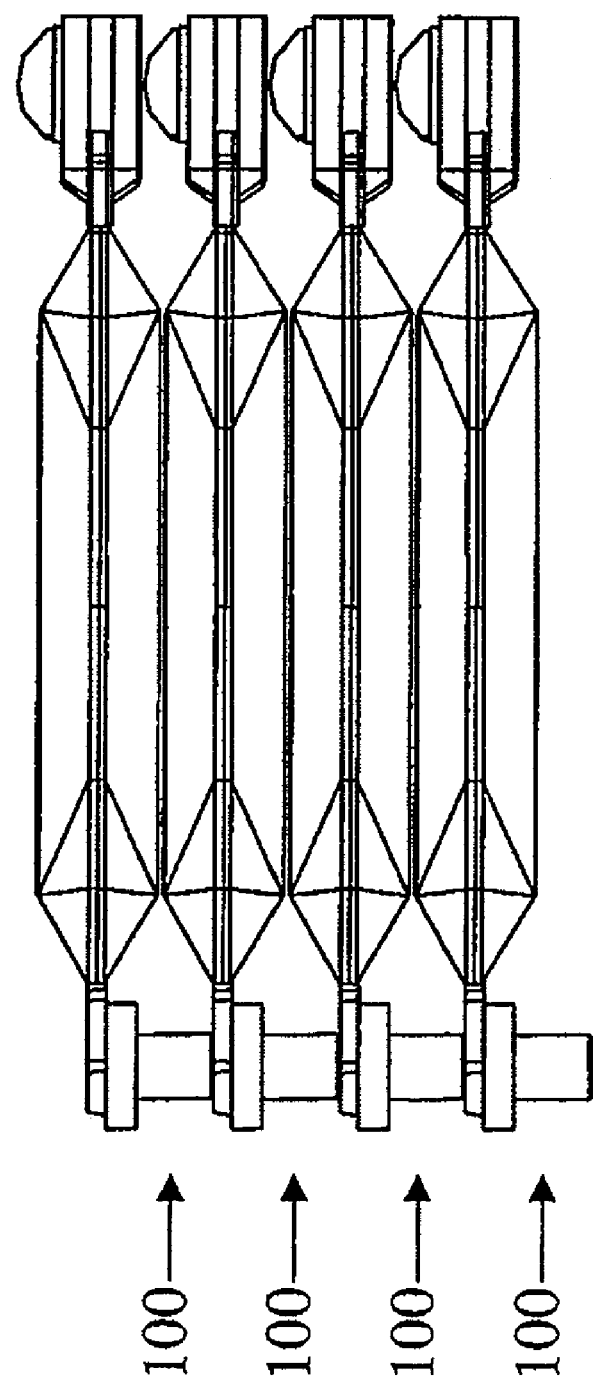
FIG. 12 shows an example of stacking or nesting devices according to one embodiment of the present invention.

FIG. 12 shows an example of stacking or nesting multiple devices 100 on top of each other. Stacking or nesting would be beneficial where space is limited, e.g. in an ambulance, and where multiple devices might be required. In one example the design and geometry of the inlet mechanism, body and/or output mechanism allows them to nest with one another. For example, the top of the output mechanism could nest into the bottom of another output mechanism (a similar nesting could be established for the input mechanism). Besides fitting the devices together, the device could also have features, e.g. ribs, indentations, Velcro, snap-mechanism, or the like, that prevent side-to-side movement. In one embodiment, the body 110 of the device 100 has dimensions of about 200-235 mm×240-290 mm×50-65 mm in a compacted configuration. In some embodiments, three devices can fit in a shelf height of no more than about 250 mm, 240 mm, 230 mm, 220 mm, 210 mm, 200 mm, 190 mm, 180 mm, 170 mm, 160 mm, 150 mm, or less.

In some embodiments, device 100 can maintain its maximum fully uncompressed volume, as well as deliver a consistent tidal (delivered) volume after being stored for a prolonged period of time. Being able to maintain this capability can be highly advantageous over current bag-type ventilators, for example, which have a relatively short shelf-life due to degradation of the bag material over time. Furthermore, use of a compression spring as a volume restoring mechanism, for example, can be advantageous as relaxation of the spring over time should not significantly affect the deliverable volume of the device. Volume delivery effected by creep or stress relaxation of components can be minimized by using an appropriate material as known in the art, such as a polymer. In some embodiments, a device 100 can be stored for at least about 1 year, 2 years, 3 years, 4 years, 5 years, 7 years, 10 years, 15 years, 20 years, 25 years, 30 years, or more while maintaining the capability to compress to a volume of less than about 35%, 30%, 25%, 20%, 15%, 10%, or less of the fully uncompressed volume of the device, as well as expand to at least about 90%, 95%, 97%, 98%, 99% or more of the fully uncompressed volume of the device prior to storage.

Figure 13C:
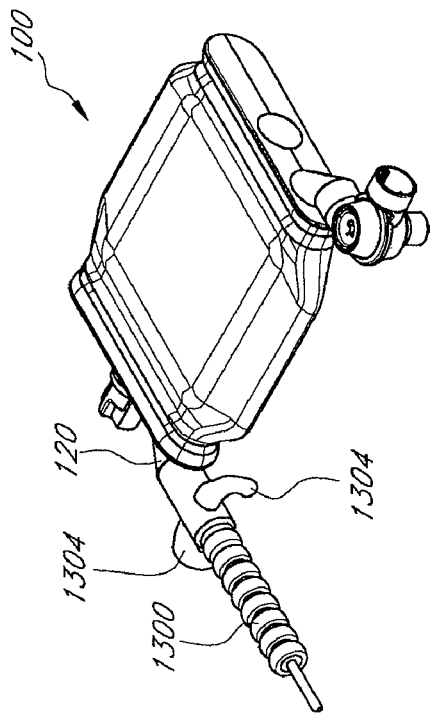
FIGS. 13A-D illustrate embodiments of visual airflow indicators that can be used with a volume-adjustable manual ventilation device, according to some embodiments of the invention.
Figure 13D:
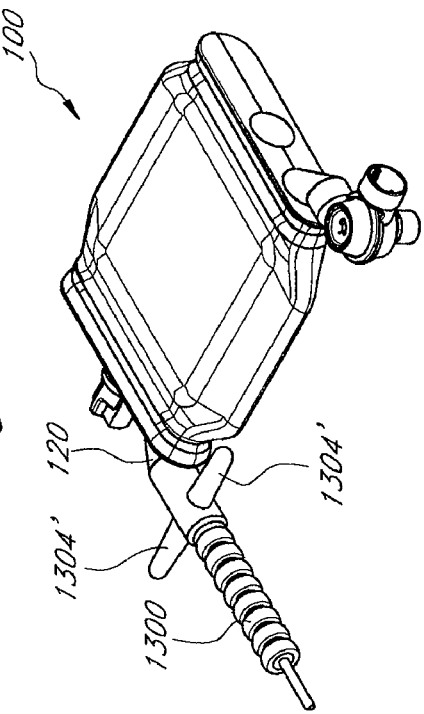
Figure 13A:
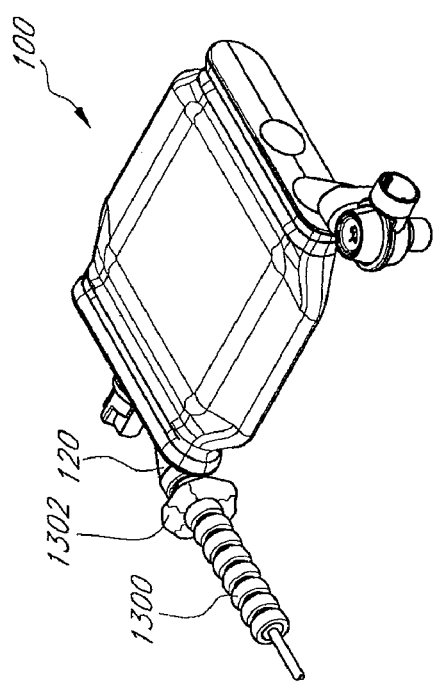
Figure 13B:
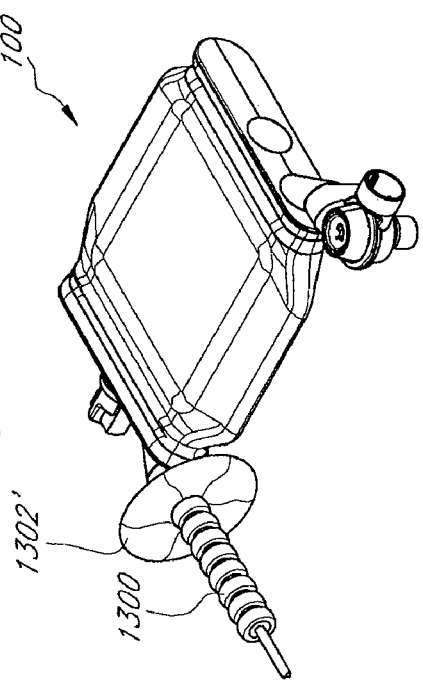

FIGS. 13A-D illustrate embodiments of visual airflow indicators that can be used with a volume-adjustable manual ventilation device, according to some embodiments of the invention. The visual airflow indicator provides a visual cue that air is flowing into the device 100 for delivery to a patient's airway. The visual airflow indicator can be operably connected to the input mechanism 120 of the device 100. The visual airflow indicator can be, in some embodiments, an expandable reservoir as part of an inflow line 1300, for example, an oxygen line or reservoir tube, and can be integrally connected to input mechanism 120 itself. The reservoir 1300 can be made of any appropriate material known in the art, such as, for example, a polymer, plastic, or rubber. FIGS. 13A-B illustrate one embodiment of a visual airflow indicator 1302, 1302' that is a circumferentially-expandable bag movable from a first deflated configuration 1302 in the absence of airflow into the input mechanism 120 (FIG. 13A) to a second inflated configuration 1302' when air is flowing into the input mechanism 120 (FIG. 13B). FIGS. 13C-D illustrate another embodiment of a visual airflow indicator 1300 that includes expandable elements 1304 that can expand radially outwardly to configuration 1304' as shown (FIG. 13D) when air is flowing into the input mechanism 120.

FIG. 14 illustrates an inflow line 1400 (e.g., an oxygen line or a reservoir tube) that may be operably connected to input mechanism 120 of device 100 and configured to allow for measuring an aspect of the patient, such as the patient's height. The patient's height, combined with knowledge of the patient's weight, or an estimation of their ideal body weight, can be used to calculate the patient's body mass index and select an appropriate volume delivery setting using the volume adjuster of the device 100. In the embodiment shown, inflow line 1400 includes markings 1402 that can define, for example, length measurements in inches or centimeters. In other embodiments, inflow line 1400 includes color-coded marking sections that correspond to colors on volume adjuster, such as adjustment dial 162. Other markings or coding systems on various elements of the device configured to measure an aspect of the patient to determine an appropriate volume (and/or frequency setting, to set an appropriate minute ventilation) can also be used, as will be appreciated by one of ordinary skill in the art.

Figure 15:
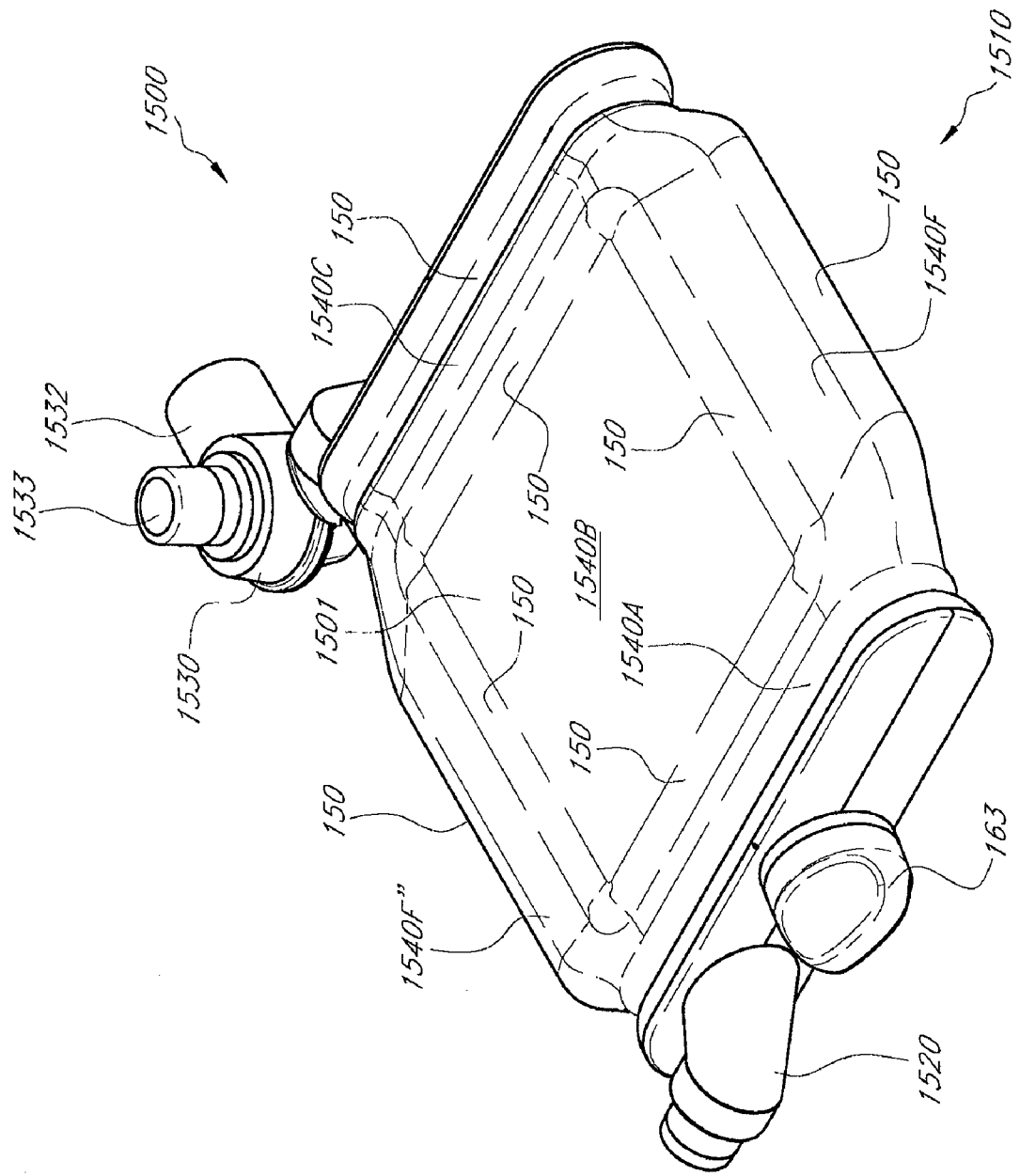
FIG. 15 is a perspective view of a ventilation device, according to one embodiment of the invention.

FIG. 15 is a perspective view of a ventilation device 1500 similar to the device 100 shown and described in connection with FIGS. 1-4. Body 1510 of device 1500 is encompassed by a covering layer 1501 (as better understood from FIG. 16) over panels 1540A, 1540B, 1540C, 1540F, 1540F" and movable structures 150 of the device 1500 (panels and movable structures are more clearly seen in FIG. 16 below), and serves to provide an air-tight seal over the body 1510 of the device 1500. Covering layer 1501 (also referred to as the skin) may be made of plastic, rubber, polymer, thermoplastic elastomer, or other suitable material as would be appreciated by one of ordinary skill in the art. Covering Layer 1501 may be slid on, adhered, co-molded, radio frequency welded, mechanically locked using rivets or screws, or otherwise attached to the body 1510 as known in the art. Covering layer 1501 can also advantageously act as a volume restoring mechanism if made of a resilient material, such as an elastomer.

Device 1500 also includes an input mechanism 1520 and output mechanism 1530 to output and deliver some or all of inputted content from body 1510 via patient connector 1533 as described in connection with FIG. 1 above, as well as adjustment dial 163. Also shown is positive end-expiratory pressure connector 1532 of output mechanism 1530 ("PEEP" connector). In contrast to the device 100 shown in FIGS. 1-4, device 1500 does not include panels 140D, 140D', 140D", 140D''', 140E, 140E', 140E", 140E''', 140G, 140G', 140G", 140G''', 140H, 140H', 140H", and 140H''' of device 100.

Figure 16:
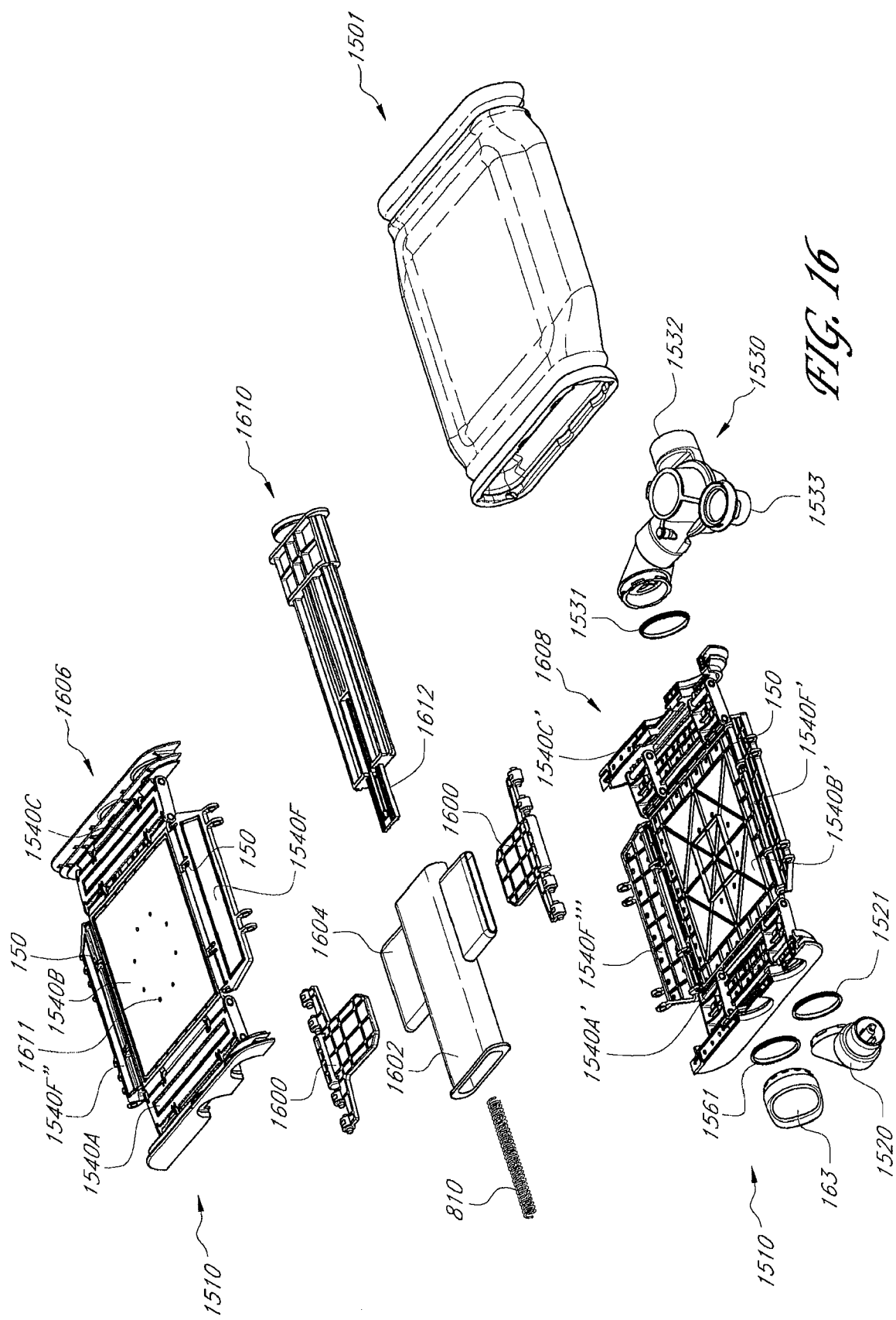
FIG. 16 is an exploded view of the ventilation device illustrated in FIG. 15.

FIG. 16 is an exploded view of the device 1500 illustrated in FIG. 15. Body 1510 of device 1500 includes first portion 1606 and second portion 1608. First portion includes a plurality of panels 1540A, 1540B, 1540C, 1540F, 1540F" operably connected by movable structures 150 that are preferably snap-fit hinges in some embodiments, as described in connection with FIG. 1 above. First 1606 and second portions 1608 also can include apertures 1611 as shown configured to receive a screw, nail, bolt, snap-on nub, or the like to connect first 1606 and second portions 1608 together and/or to the covering layer 1501. Also illustrated is output mechanism 1530 and patient connector 1533 as previously described, and attached to body 1510 via element 1531 which can be a seal, gasket, or the like. Input mechanism 1520 and adjustment dial 163 can also be as previously described, and can be connected to body 1510 via elements 1521 and 1561, respectively. Elements 1521, 1561 may be seals, gaskets, and the like similar to element 1531. Adjustment dial 163 shown rotates in a plane perpendicular to main slider 1610 with narrowed end 1612, although it can also rotate parallel, or in other orientations to main slider 1610 as well in other embodiments. As described in connection with FIG. 7 above, other volume adjusters known in the art may be used as well.

Second portion 1608 of body 1510 includes panels 1540A', 1540B', 1540C', 1540F', and 1540F''' also connected by movable structures 150. Also illustrated is main slider 1610 which can include elements of main shaft 610 and receiving shaft 620 as described in connection with volume adjuster and volume restoring mechanism and FIGS. 7-8 above. Main slider 1610 movably resides within main slider housing 1602. Element 810 shown is a spring, preferably a compression spring as part of volume restoring mechanism as described in connection with FIG. 8 above.

Also shown in FIG. 16 are side sliders 1600 connected to panels 1540F, 1540F' and panels 1540F", 1540F''' by movable structures 150, e.g., snap-fit hinges. Side sliders 1600 movably reside within side slider housing 1604, and structurally stabilize the device 1500 during actuation, as better illustrated in FIGS. 17-18 below.

FIG. 17A is a side view of device 1500 in an uncompressed state with covering layer 1501 removed for clarity. Shown are input mechanism 1520, output mechanism 1530 with patient connector 1533 and PEEP connector 1532, and panels 1540A, 1540A', 1540C, 1540C', 1540F and 1540F' operably connected to adjacent panels by hinges 150 as previously described. FIG. 17B shows the device of FIG. 17A (with covering layer 1501) in a compressed state.

FIGS. 18A-B are top horizontal sectional views of device 1500 in uncompressed and compressed states, respectively. As shown (and perhaps better seen in FIGS. 19A-B), side sliders 1600 move medially toward each other as the device 1500 moves from the uncompressed to the compressed state, while narrow end 1612 within main slider 1610 moves into slot 750 (and slot 750', not shown) of adjustment dial 163. Exertion of a compressive force (e.g., by manual pressure on one or more panels) on device 1500 will result in a buildup of force within spring 810 (which is preferably a compression spring in this embodiment) and result in restoring the body 1510 back to an uncompressed state when the compressive force is released.

FIG. 19A is a vertical sectional view of device 1500 through line 19A-19A of FIG. 18A. FIG. 19B is a vertical sectional view of device 1500 through line 19B-19B of FIG. 18B. Shown are panels 1540A, 1540A', 1540B, 1540B', 1540C and 1540C' operably connected to adjacent panels by hinges 150 as previously described. As noted above, as device 1500 moves from the uncompressed (FIG. 19A) to the compressed (FIG. 19B) state, narrow end 1612 of main slider 1610 will move into slot 750 (and slot 750', not shown) of adjustment dial 163. As will be readily appreciated by one of ordinary skill in the art and described in connection with FIG. 7A above, tidal volume delivered by device 1500 can be readily adjusted by actuating adjustment dial 163 in an appropriate direction, thus changing to a different slot with a different length and distance traveled by main shaft 610 from the uncompressed to the compressed state.

Figure 20B:
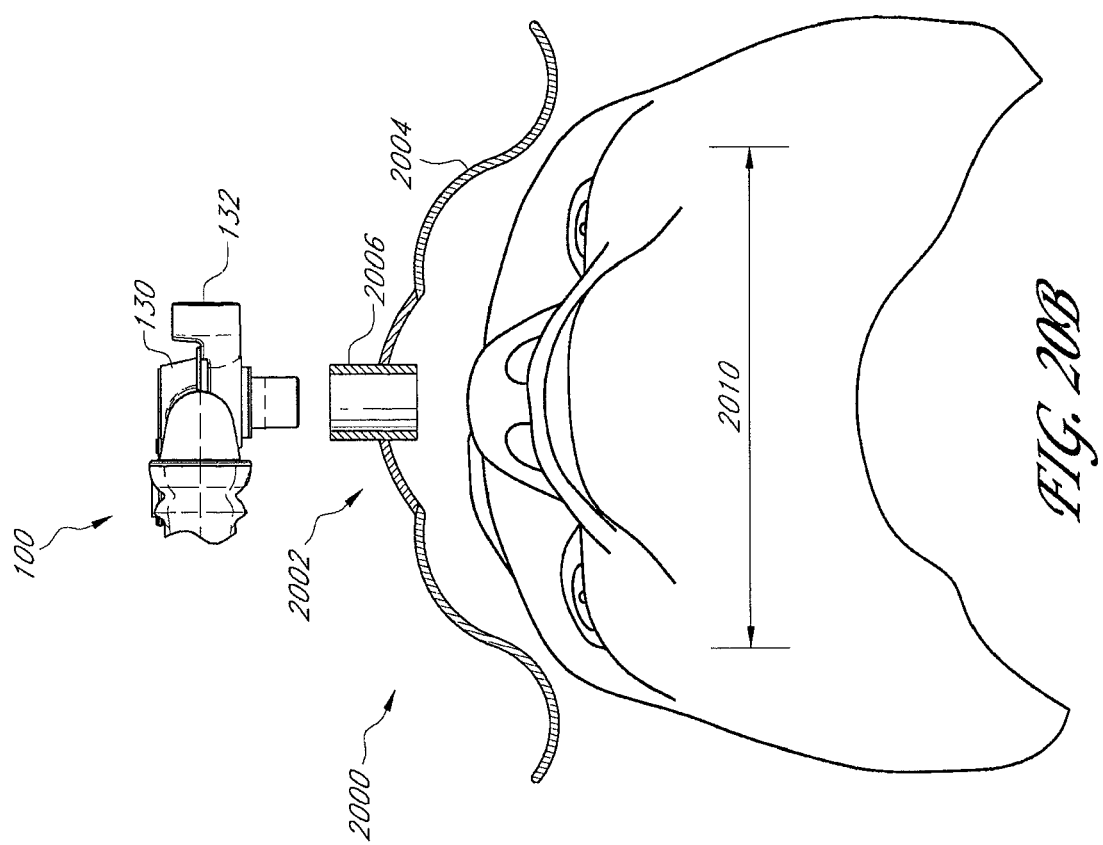
Figure 20A:
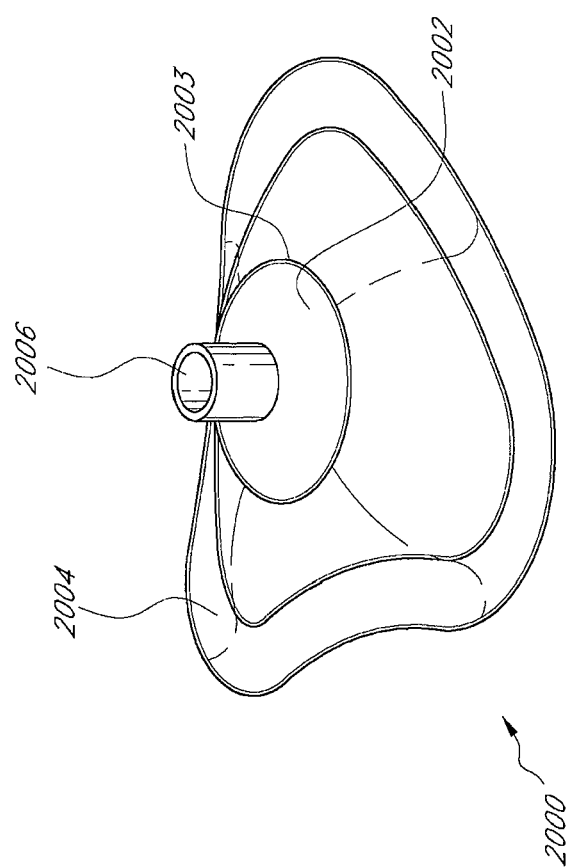

FIGS. 20A-D illustrate a face mask 2000 that can be used with a ventilation device, according to one embodiment of the invention. A single face mask can advantageously be adapted for both adult and pediatric uses, obviating the need for two separate masks. As shown in FIG. 20A, face mask 2000 includes an outer portion 2004 and an inner portion 2002. The inner portion 2002 is most preferably a bi-stable cone configured to move from a first stable position 2002 to a second stable position 2002'. In doing so, the bi-stable cone 2002 is displaced vertically, creating linear movement. In a preferred embodiment, the first stable position 2002 will allow the mask 2000 to generally fit over an adult airway while the second stable position 2002' will allow the mask 2000 to generally fit over a pediatric airway. The outer diameter 2003 of cone 2002 is preferably substantially circular, oval, or the like, although other possible shapes for the outer diameter 2003 can also be readily envisioned. The bi-stable cone also has an inlet portion 2006 that may interface with, for example, an outlet of a ventilator or an oxygen line, such as patient port 1533.

Face mask 2000 can be transformed from an first configuration for adult use to a second configuration for pediatric use in the following manner. FIG. 20B illustrates a vertical sectional schematic view of face mask 2000 positioned over an adult patient's face. Face mask 2000 is shown operably connected at inlet portion 2006 to connector 132 of outlet 130 of ventilation device 100. A first length 2010 of mask 2000 that spans a length over adult patient's face is shown. To transform the mask 2000 for pediatric use, an operator can apply pressure to bi-stable cone 2000 to move cone 2000 from first stable position 2002 (shown in phantom) to second stable position 2002' as shown in FIG. 20C. Next, mask 2000 is turned over as shown in FIG. 20D. Once turned over, mask 2000 has a second length 2008 that spans a length over pediatric patient's face as shown; second length 2008 is less than first length 2010. One of ordinary skill in the art will readily appreciate that the mask can also readily be transformed from the pediatric configuration to the adult configuration by performing the steps illustrated in reverse.

Figure 21B:
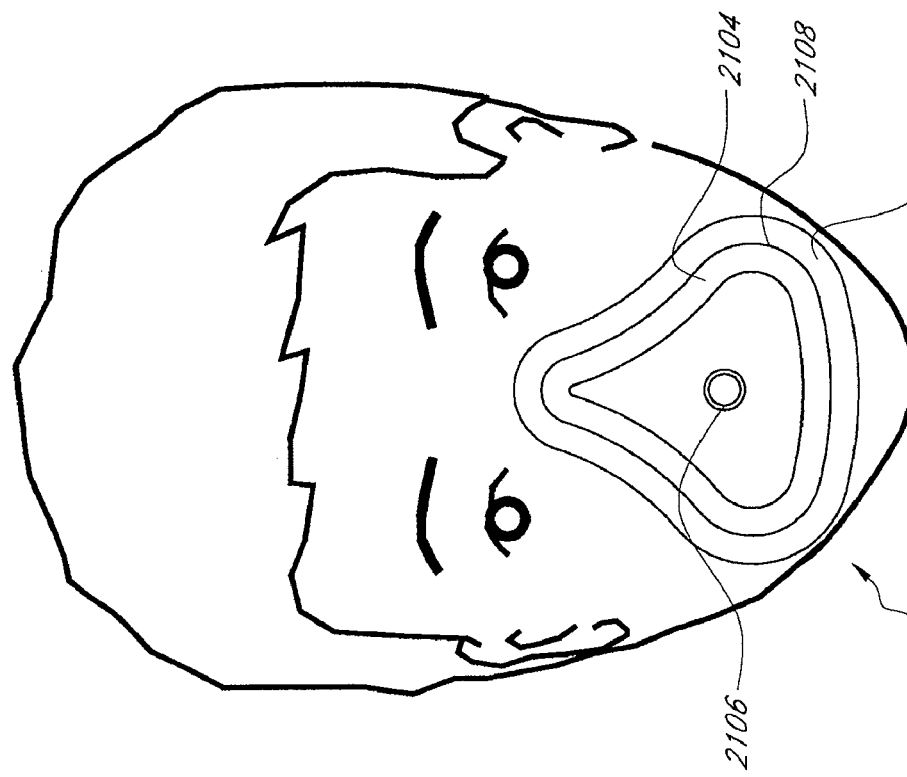
Figure 21A:
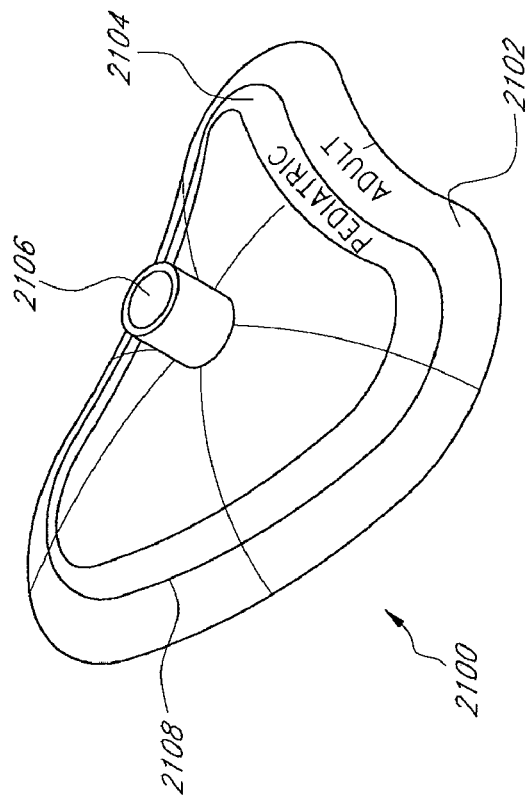

FIGS. 21A-C depict another face mask that can be used with a ventilation device, according to one embodiment of the invention. As shown in FIG. 21A, face mask 2100 includes outer portion 2102, inner portion 2104, and inlet 2106. Outer portion 2102 and inner portion 2104 are operably connected by seam 2108. Seam is preferably made of a tear-away material configured to facilitate tearing of inner portion 2104 from outer portion 2102. In some embodiments, the seam 2108 has thinned walls or perforations to facilitate tearing. In other embodiments, seam 2108 includes an adhesive material to facilitate tearing. Other tear-away materials known in the art can also be utilized as well. FIG. 21B depicts mask 2100 situated on an adult patient. Face mask 2100 can be transformed from an adult configuration 2100 to a pediatric configuration 2100' by separating (e.g., by pulling apart) outer portion 2102 from inner portion 2104. Pediatric configuration 2100' and separated outer portion 2102 are shown in FIG. 21C. The masks described in connection with FIGS. 21-22 can, for example, have a length of no more than about 135 mm, preferably between about 115-135 mm, and a width of no more than about 115 mm, preferably between about 100-115 mm in an adult configuration of some mask embodiments. A pediatric configuration can, for example, have a length of no more than about 115 mm, preferably between about 75-115 mm, and a width of no more than about 100 mm, preferably between about 70-100 mm.

Figure 22A:
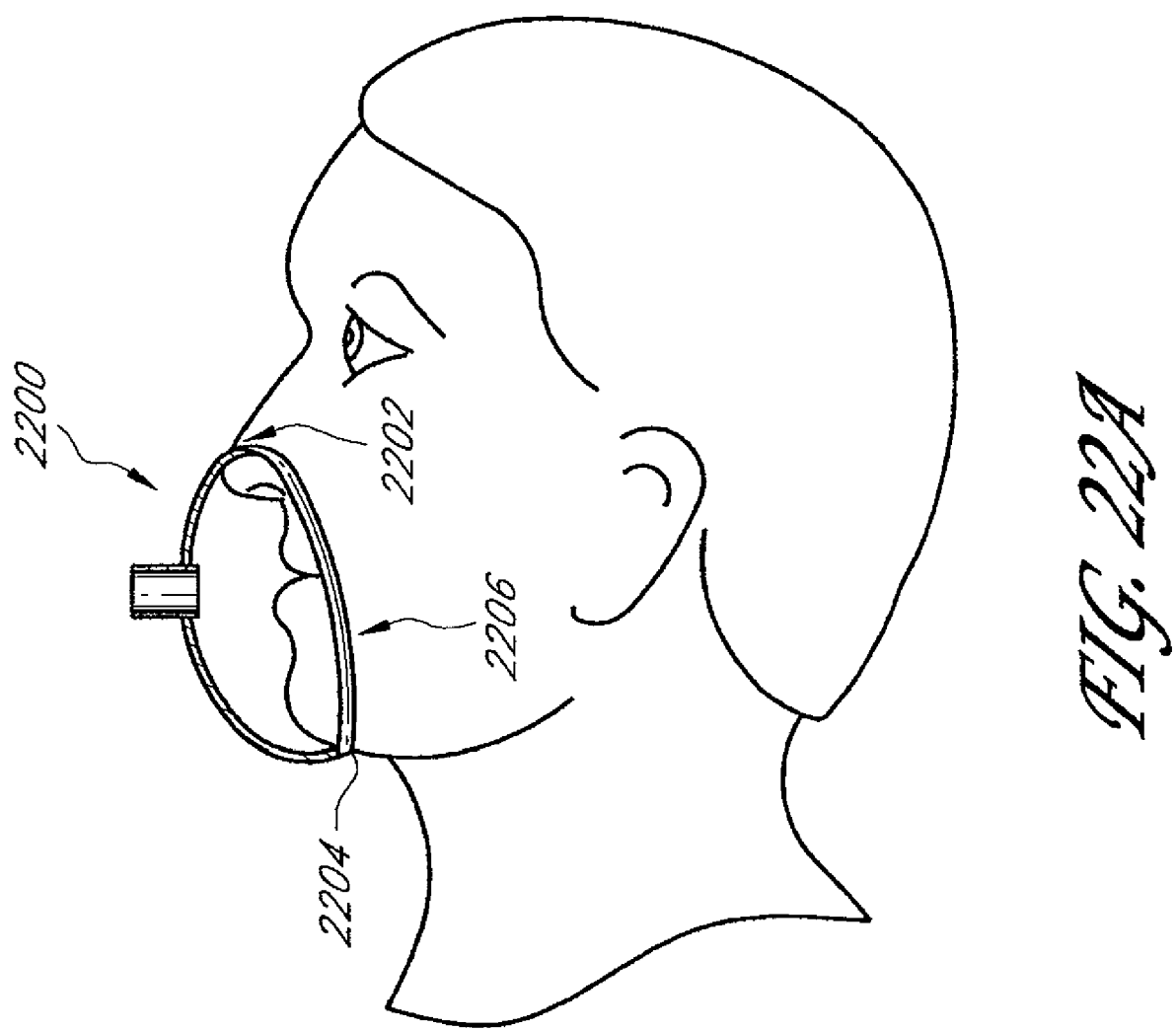
FIGS. 22A-C illustrate an embodiment of a face mask that is shaped and configured to create a sealing surface extending from cephalad at the base of the nose near the alar sidewalls to caudally under the mandible as shown.
Figure 22C:
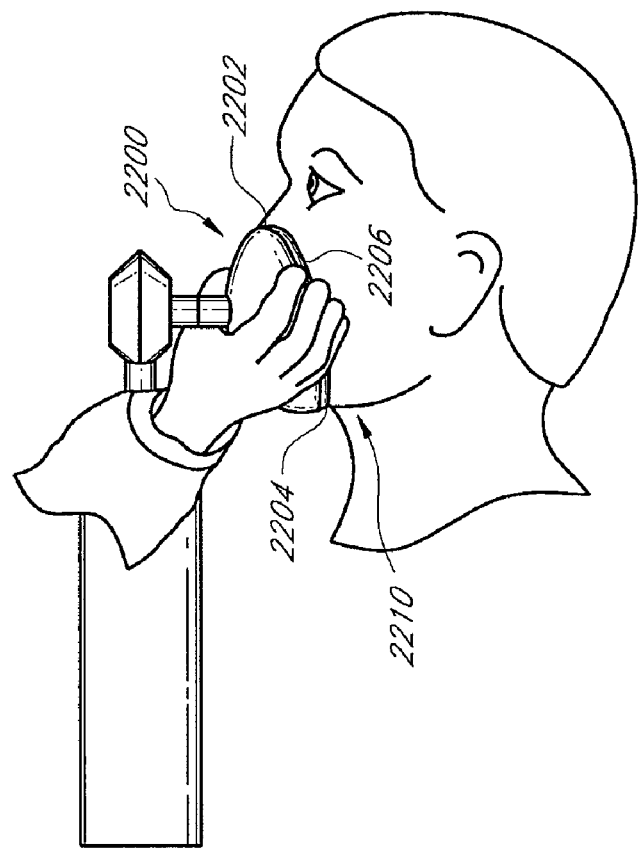
Figure 22B:
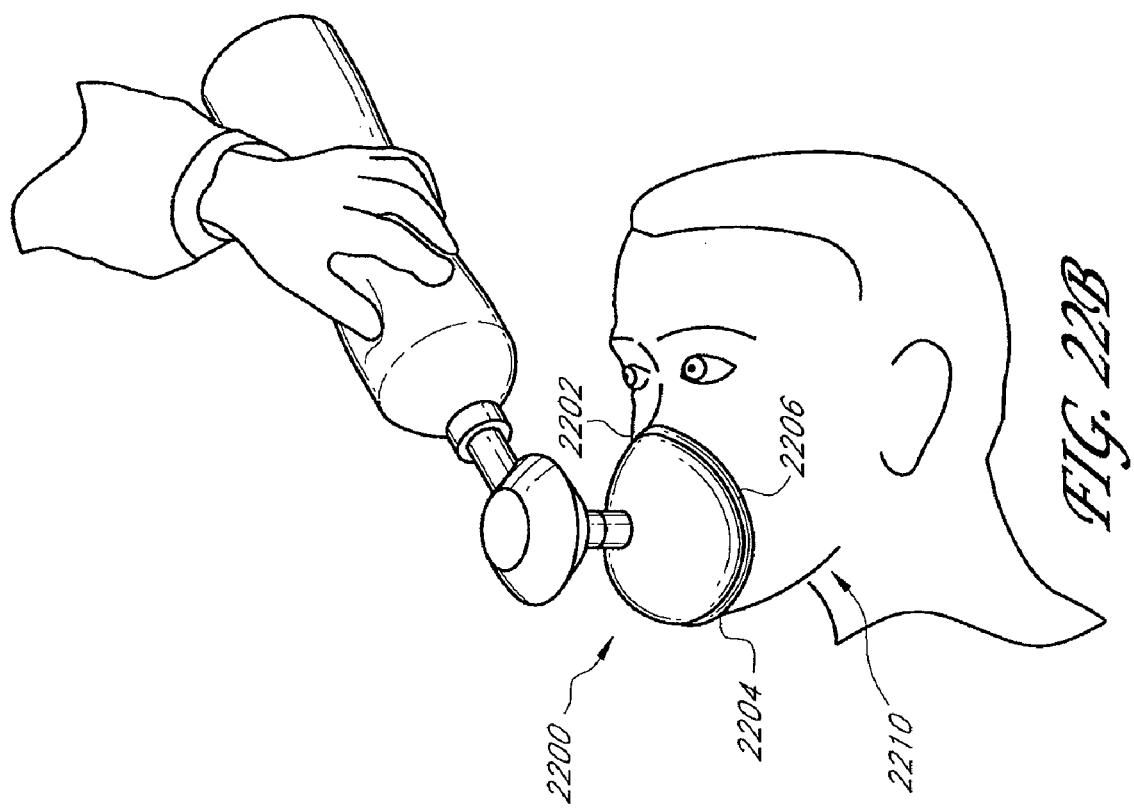

FIGS. 22A-C illustrate an embodiment of a face mask 2200 that is shaped and configured to create a sealing surface extending generally (near dotted line 2206) from cephalad at the base of the nose 2202 near the alar sidewalls to caudally under the mandible 2204 as shown. Conventional masks are generally configured to create a sealing surface cephalad from the nasion to caudal on the mandible. Application of mask 2200 can advantageously create an improved sealing surface over conventional masks, and thus improved ventilation of a patient, especially when combined with a jaw thrust maneuver as known in the art. In some embodiments, the head-tilt chin-lift maneuver, as known in the art, can be substituted for the jaw thrust maneuver. The jaw thrust maneuver is typically performed on a supine patient by kneeling down at the patient's head and grasping the posterior aspects of the mandible with the fingers of both hands (with the thumbs at the chin) and lifting up. When the mandible is displaced forward, it pulls the tongue forward and prevents it from occluding the entrance to the trachea, helping to ensure a patent airway. FIGS. 22B and 22C illustrate different schematic perspective views of mask 2200 on the patient. A jaw thrust can be performed submandibularly by applying a force as shown by arrow 2210.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For all of the embodiments described above, the steps of the methods need not be performed sequentially.

What is claimed is:

1. A manually operable volume-adjustable ventilation device, comprising:
a reservoir with an inlet mechanism, an outlet mechanism, and a volume adjuster configured to move a volume adjustment limit of the reservoir and change an expressed maximum volume of the reservoir;
wherein said reservoir comprises a body having a plurality of movable walls defining an enclosed volume; wherein said reservoir has an uncompressed state and a compressed state; wherein said walls are movable with respect to each other, such that moving said walls expresses the volume adjustment limit of the reservoir; wherein said walls are operably connected by movable structures; wherein a first wall and a second wall rotate about a first axis, and wherein a third wall rotates around a second axis wherein said second axis is substantially orthogonal to said first axis when the reservoir moves from an uncompressed to a compressed state.

2. The device of claim 1, wherein the movable structures are hinges.

3. The device of claim 1, wherein the movable structures and the movable walls are co-molded together.

4. The device of claim 1, further comprising a covering layer over the body of the reservoir of the device.

5. The device of claim 4, wherein the covering layer is a slide-on skin.

6. The device of claim 4, wherein the covering layer is co-molded or adhered to the walls.

7. The device of claim 1, wherein the device is configured such that applying a force to at least one of the walls of the reservoir will result in the reservoir moving from the uncompressed state to a fully compressed state.

8. The device of claim 1, wherein the device is configured such that an expressed volume of the device for a given adjustment limit is consistently no more than about 10 cc of a disclosed volume setting on the volume adjuster from compression to compression for a given force of compression and airway resistance of a patient.

9. The device of claim 1, further comprising a volume restoring mechanism to restore said reservoir from said compressed state to said uncompressed state.

10. The device of claim 9, wherein the volume restoring mechanism is selected from the group consisting of: a compression spring, an extension spring, and a resilient covering layer.

11. The device of claim 1, wherein the volume adjuster comprises a stop dial.

12. The device of claim 1, further comprising a frequency adjuster to adjust the time to restore said reservoir from said compressed state to said uncompressed state.

13. The device of claim 1, further comprising a frequency adjuster to adjust the time to compress said reservoir from said uncompressed state to said compressed state.

14. The device of claim 1, wherein the device is configured such that the maximum change in said expressed volume of the reservoir is no more than about 1400 cc.

15. The device of claim 1, wherein the device is configured such that the maximum change in said expressed volume of the reservoir is no more than about 250 cc.

16. The device of claim 1, further comprising tactile feedback areas on one or more of said walls.

17. The device of claim 16, wherein said tactile feedback areas are flexible areas and sized and positioned to fit a thumb of a hand or one or more fingers of said hand.

18. The device of claim 1, further comprising a visual feedback mechanism.

19. The device of claim 18, wherein the visual feedback mechanism is an expandable air reservoir operably connected to said inlet mechanism of said device; said air reservoir having an expandable wall configured to indicate the presence of air flow through the reservoir.

20. The device of claim 1, further comprising an audible feedback mechanism.

21. The device of claim 20, wherein said audible feedback mechanism is a pop-off valve.

22. The device of claim 1, further comprising an air filter operably connected to the inlet.

23. The device of claim 1, further comprising an inflow line with measurement markings to measure an aspect of the patient and estimate an appropriate expressed volume based on the measurement.

24. The device of claim 1, wherein the device can be compressed in a stored configuration to less than 35% of a fully expanded volume of the device; wherein said device is configured to deliver at least 95% of the fully expanded volume of the device after being stored for at least about 3 years.

25. The device of claim 1, wherein a device is configured such that three devices can be stacked in a shelf with a shelf height of no more than about 180 mm.

26. The device of claim 1, wherein a device has a height of no more than about 70 mm and a side panel width of no more than about 50 mm to allow the device to be comfortably compressed in one hand by an operator.

27. A medical system comprising: the ventilation device of claim 1; and a face mask.

28. A method of ventilating a patient, comprising:
providing a ventilation device comprising a reservoir with an inlet mechanism, an outlet mechanism, and a volume adjuster configured to move a volume adjustment limit of the reservoir and change an expressed maximum volume of the reservoir;
wherein said reservoir comprises a body having a plurality of movable walls defining an enclosed volume; wherein said reservoir has an uncompressed state and a compressed state; wherein said walls are movable with respect to each other, such that moving said walls expresses the volume adjustment limit of the reservoir; wherein said walls are operably connected by movable structures; wherein a first wall and a second wall rotate about a first axis, and wherein a third wall rotates around a second axis wherein said second axis is substantially orthogonal to said first axis when the reservoir moves from an uncompressed to a compressed state; connecting the inlet of the device to an air or oxygen source;
connecting the outlet of the device to a mask or tube configured to interface with a patient's airway; and
actuating the device from an uncompressed state to a compressed state by applying a force to at least one wall of the device.

29. The method of claim 28, further comprising the step of releasing the force to allow the reservoir to move back from the compressed state to the uncompressed state.

30. The method of claim 29, wherein the reservoir moves back from the compressed state to the uncompressed state by the action of a volume restoring mechanism.

31. The method of claim 30, wherein the volume restoring mechanism is selected from the group consisting of: a compression spring, an extension spring, and a resilient covering layer.

32. The method of claim 28, wherein the movable structures are hinges.

33. The method of claim 28, wherein the movable structures and the walls are co-molded or adhered together.

34. The method of claim 28, wherein the device is configured such that applying a force to at least one of the walls of the reservoir will result in the reservoir moving from the uncompressed state to a fully compressed state.

35. The method of claim 28, further comprising selecting an appropriate expressed maximum volume setting from the volume adjuster.

36. The method of claim 28, further comprising the step of adjusting the time to restore said reservoir from said compressed state to said uncompressed state.

37. The method of claim 28, further comprising the step of adjusting the time to compress said reservoir from said uncompressed state to said compressed state.

38. The method of claim 28, wherein the device is configured such that the maximum change in said expressed volume of the reservoir is no more than about 1400 cc.

39. The method of claim 28, further comprising observing a visual feedback mechanism that indicates the presence of airflow into the device.

40. The method of claim 39, wherein the visual feedback mechanism is an air reservoir with an expandable wall configured to indicate the presence of air flow through the reservoir.

41. The method of claim 28, further comprising the step of listening to an audible feedback mechanism that provides feedback over one or more of the group consisting of: the compression speed, frequency, and expressed volume of the device.

42. The method of claim 28, further comprising the step of filtering air before air enters the body of the device.

* * * * *

UNITED STATES PATENT AND TRADEMARK OFFICE
CERTIFICATE OF CORRECTION

PATENT NO. : 7,658,188 B2  Page 1 of 1
APPLICATION NO. : 11/635381
DATED : February 9, 2010
INVENTOR(S) : Halpern It is certified that error appears in the above-identified patent and that said Letters Patent is hereby corrected as shown below:

On the Title page, Item (75) Inventors, please delete "Stephen Ruoss, Redwood City, CA (US)"

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO.        : 7,658,188 B2
APPLICATION NO.   : 11/635381
DATED             : February 9, 2010
INVENTOR(S)       : Halpern et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 734 days.

Signed and Sealed this

Twenty-eighth Day of December, 2010

David J. Kappos
*Director of the United States Patent and Trademark Office*